(12) United States Patent
Qi et al.

(10) Patent No.: US 9,957,287 B2
(45) Date of Patent: *May 1, 2018

(54) METHODS AND COMPOSITIONS TO TREAT TYPE-1 AND TYPE-2 DIABETES

(71) Applicant: CORNELL UNIVERSITY, Ithica, NY (US)

(72) Inventors: Ling Qi, Ann Arbor, MI (US); Shengyi Sun, Dallas, TX (US); Yewei Ji, Ann Arbor, MI (US)

(73) Assignee: CORNELL UNIVERSITY, Ithaca, NY (US)

( * ) Notice: Subject to any disclaimer, the term of this patent is extended or adjusted under 35 U.S.C. 154(b) by 0 days. days.

This patent is subject to a terminal disclaimer.

(21) Appl. No.: 15/604,201

(22) Filed: May 24, 2017

(65) Prior Publication Data

US 2017/0342097 A1   Nov. 30, 2017

Related U.S. Application Data

(60) Provisional application No. 62/341,716, filed on May 26, 2016.

(51) Int. Cl.

| A61K 48/00 | (2006.01) |
| A61K 31/66 | (2006.01) |
| A61K 31/215 | (2006.01) |
| A61K 31/165 | (2006.01) |
| C07F 9/10 | (2006.01) |
| G01N 33/49 | (2006.01) |
| G01N 33/50 | (2006.01) |
| A61K 31/685 | (2006.01) |
| A61K 31/661 | (2006.01) |
| A61K 35/12 | (2015.01) |
| A61K 31/625 | (2006.01) |
| A61K 31/222 | (2006.01) |
| C12N 15/86 | (2006.01) |

(52) U.S. Cl.
CPC .............. *C07F 9/10* (2013.01); *A61K 31/222* (2013.01); *A61K 31/625* (2013.01); *A61K 31/661* (2013.01); *A61K 31/685* (2013.01); *A61K 35/12* (2013.01); *A61K 48/00* (2013.01); *G01N 33/49* (2013.01); *G01N 33/507* (2013.01); *C12N 15/86* (2013.01); *G01N 2800/042* (2013.01)

(58) Field of Classification Search
CPC ...... A61K 48/00; A61K 31/66; A61K 38/671; A61K 31/165
USPC .......................... 424/93.2; 514/114, 529, 618
See application file for complete search history.

(56) References Cited

U.S. PATENT DOCUMENTS 9,517,993 B2   12/2016   Yin et al.
2009/0105314 A1   4/2009   Li et al.

FOREIGN PATENT DOCUMENTS

WO   WO 2004/098646 A1   11/2004

OTHER PUBLICATIONS

Meivar-Levy, I. et al., "Stem Cell Research—Regenerative Medicine: Using Liver to Generate Pancreas for Treating Diabetes", IMAJ, (Jun. 2006), vol. 8, pp. 430-434.

(Continued)

*Primary Examiner* — Raymond J Henley, III
(74) *Attorney, Agent, or Firm* — Scully Scott Murphy & Presser

(57) ABSTRACT

The present disclosure is directed to novel methods of treating type-1 or type-2 diabetes by inactivating TLR2 and TLR4 genes together in cells capable of producing insulin and/or regenerating β cells, and providing the cells to a subject in need thereof.

21 Claims, 15 Drawing Sheets
(15 of 15 Drawing Sheet(s) Filed in Color)

(56) References Cited

OTHER PUBLICATIONS

"Method to Target TLR2/4 Signaling Pathways for the Control of Beta Cell Proliferation in the Treatment of Diabetes", http://www.flintbox.com/public/project/25822, (Jul. 29, 2014), 3 pages.

Benitez, C.M. et al., "An Integrated Cell Purification and Genomics Strategy Reveals Multiples Regulators of Pancreas Development", PLOS Genetics, (Oct. 2014), vol. 10, Issue 10, pp. 1-15.

Cani, P.D. et al., "Changes in Gut Microbiota Control Metabolic Endotoxemia-Induced Inflammation in High-Fat Diet-Induced Obesity and Diabetes in Mice", Diabetes, (Jun. 2008), vol. 57, pp. 1470-1481.

Cani, P.D. et al., "Metabolic Endotoxemia Initiates Obesity and Insulin Resistance", Diabetes, (Jul. 2007), vol. 56, pp. 1761-1772.

Donath, M.Y. et al., "Inflammation in Obesity and Diabetes: Islet Dysfunction and Therapeutic Opportunity", Cell Metabolism, (Jun. 4, 2013), pp. 861-872.

Ji, Y. et al., "Diet-Induced Alterations in Gut Microflora Contribute to Lethal Pulmonary Damage in TLR2/TLR4-Deficient Mice", Cell Reports, (Jul. 10, 2014), vol. 8, pp. 137-149.

Jourdan, T. et al., "Activiation of the NIrp3 inflammasome in infiltrating macrophages by endocannabinoids mediates beta cell loss in type 2 diabetes", Nat. Med. (Sep. 2013), vol. 19, No. 9, pp. 1132-1140.

Lee, J. et al., "Expansion and conversion of human pancreatic ductal cells into insulin-secreting endocrine cells", eLIFE, (2013), pp. 1-22.

Nir, T. et al., "Recovery from diabetes in mice by Beta cell regeneration", The Journal of Clinical Investigation, (Sep. 2007), vol. 117, No. 9, pp. 2553-2561.

Shi, H. et al., TLR4 links innate immunity and fatty acid-induced insulin resistance, The Journal of Clinical Investigation, (Nov. 2006), vol. 116, No. 11, pp. 3015-3025.

Sun, S. et al., "Mechanisms of Inflammatory Responses in Obese Adipose Tissue", Annu Rev Nutr., (Aug. 21, 2012), vol. 32, pp. 261-286.

Xiao, X. et al., "No evidence for Beta cell neogenesis in murine adult pancreas", The Journal of Clinical investigation, (May 2013), vol. 123, No. 5, pp. 2207-2217.

METHODS AND COMPOSITIONS TO TREAT TYPE-1 AND TYPE-2 DIABETES

CROSS REFERENCE TO RELATED APPLICATION

This application claims the benefit of priority from U.S. Provisional Application No. 62/341,716, filed May 26, 2016, the entire contents of which are incorporated herein by reference.

INCORPORATION BY REFERENCE OF SEQUENCE LISTING

The Sequence Listing in an ASCII text file, named as 33536_SEQ_ST25.txt of 7 KB, created on May 22, 2017, and submitted to the United States Patent and Trademark Office via EFS-Web, is incorporated herein by reference.

FIELD OF THE DISCLOSURE

The present disclosure relates to inactivating toll-like receptor (TLR) 2 and 4 genes in β cells capable of producing insulin to promote β cell proliferation and regeneration for the treatment of type-1 (T1D) or type-2 diabetes (T2D).

BACKGROUND

β cell replacement and regeneration therapies are promising approaches for the treatment of insulin-dependent type 1 (T1D) and type 2 diabetes (T2D) (Stewart, A. F. et al., *Diabetes* 64, 1872-1885 (2015); Wang, P. et al., *Nature Reviews Endocrinology*, 11, 201-212 (2015)). In rodents and humans, β cells are derived largely from two processes: neogenesis of β cells from ductal precursor cells, and replication of preexisting β cells (Dor, Y. et al., *Nature* 429, 41-46 (2004); Xu, X. et al., *Cell*, 132, 197-207 (2008); Garofano, A. et al.,*FASEB J.*, 14, 2611-2617 (2000)). Neogenesis mostly occurs during fetal and neonatal life, whereas mitotic expansion of β cells in adults compensates for increased metabolic demands (Garofano, A. et al., *FASEB J.*, 14, 2611-2617 (2000); Teta, M. et al., *Diabetes* 54, 2557-2567 (2005); Meier, J. J. et al., *Diabetes* 57, 1584-1594 (2008); Nir, T. et al., *J Clin Invest*, 117, 2553-2561 (2007); Lee, J. et al., eLife 2, e00940 (2013); Xiao, X. et al., *J Clin Invest*, 123, 2207-2217 (2013)). However, most adult pancreatic β cells are refractory to cell cycle entry and proliferation and remain in a state of senescence.

Of a dozen distinct TLR proteins, TLR2 and TLR4 are best known for their roles in the induction of innate and adaptive immune responses against all known pathogens such as viruses, fungi, bacteria, and protozoa (Lemaitre, B., Nicolas, E., Michaut, L., Reichhart, J. M. et al., *Cell* 86, 973-983 (1996); Medzhitov, R. et al., *Nature* 388, 394-397 (1997); Poltorak, A. et al., *Science* 282, 2085-2088 (1998)). Both gut microbiota derivatives such as LPS and LTA (Cani, P. D. et al.,*Diabetes* 56, 1761-1772 (2007); Cani, P. D. et al., *Diabetes* 57, 1470-1481 (2008)) and fatty acids (Shi, H. et al., *J Clin Invest* 116, 3015-3025 (2006)) are likely endogenous ligands of TLR2 and TLR4. Despite intense research efforts from many laboratories, there is no overall consensus regarding the role of TLR2 and TLR4 in metabolism and in β cell function (Sun, S. et al., *Annu Rev Nutr* 32, 261-286 (2012); Donath, M. Y. et al., *Cell Metab* 17, 860-872 (2013)). Indeed, Tlr2 and Tlr4 single knockout mice exhibit mild and similar metabolic phenotypes, which were thought to be likely due to their redundant and compensatory functions (Lee, C. C. et al., *Nat Rev Immunol*, 12, 168-179 (2012)).

SUMMARY OF THE DISCLOSURE

In one aspect, this disclosure provides a method of treating diabetes in a subject comprising providing insulin-producing cells to the subject, wherein the TLR2 and TLR4 genes in said cells have been inactivated In some embodiments, the cells are provided by obtaining insulin-producing cells, inactivating the TLR2 and TLR4 genes in the obtained cells ex vivo, and transplanting the cells into the subject.

In some embodiments, the cells are provided by inactivating the TLR2 and TLR4 genes in insulin-producing cells in the subject in vivo.

In some embodiments, the insulin-producing cells are cells of a pancreatic tissue.

In some embodiments, the insulin-producing cells are provided to the subject in the form of a pancreas, pancreatic islets or pancreatic β cells.

In some embodiments, the insulin-producing cells are derived from stem cells.

In some embodiments, stem cells are selected from the group consisting of pancreatic stem cells, adult stem cells, induced pluripotent stem cells, embryonic stem cells, umbilical cord blood cells, amnion cells, placenta cells, umbilical cord vein cells, umbilical cord matrix cells, and progenitor-like stem cells.

In some embodiments, the insulin-producing cells are derived from non-pancreatic cells. In some embodiments, the non-pancreatic cells are liver cells.

In some embodiments, the insulin-producing cells (e.g., such as cells derived from stem cells or cells derived from non-pancreatic cells) are further induced to express PDX-1.

In some embodiments, the inactivation of the TLR2 and TLR4 genes in cells is achieved by deleting or mutating the TLR2 and TLR4 genes in whole or in part such that no functional TLR2 or TLR4 protein product is expressed.

In some embodiments, the inactivation of the TLR2 and TLR4 genes in cells is achieved by a method selected from the group consisting of CRISPR/Cas system, Cre/Lox system, TALEN system and homologous recombination.

In some embodiments, the inactivation of the TLR2 and TLR4 genes in cells is achieved by blocking the signaling of TLR2 and TLR4 using an oxidized phospholipid.

In some embodiments, the phospholipid has the following chemical structure:

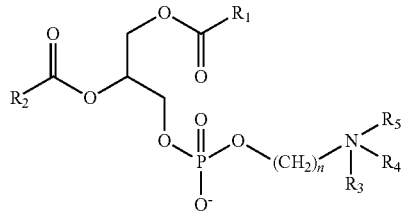

wherein:

$R_1$ is $C_{10}$-$C_{22}$ alkyl;

$R_2$ is $C_{10}$-$C_{22}$ alkenyl having 1-6 double bonds;

$R_3$, $R_4$ and $R_5$ are independently hydrogen or $C_1$-$C_{12}$ alkyl; and n is an integer from 1-4.

In some embodiments, the phospholipid has the following chemical structure:

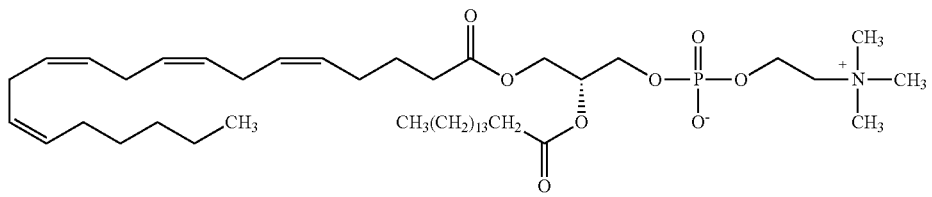

In some embodiments, the inactivation of the TLR2 and TLR4 genes in cells is achieved by blocking the signaling of TLR2 and TLR4 using a combination of a TLR2 inhibitory compound and a TLR4 inhibitory compound.

In some embodiments, the TLR2 inhibitory compound has the following chemical structure:

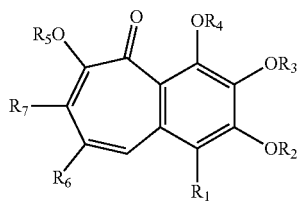

wherein:
$R_1$ and $R_7$ is hydrogen or $C_1$-$C_{12}$ alkyl;
$R_2$, $R_3$, $R_4$ and $R_5$ $R_5$ are independently hydrogen, $C_1$-$C_{12}$ alkyl, or $C_3$-$C_{12}$ cyclocakyl;
$R_6$ is $COOR_8$, $CONHR_8$; and
$R_8$ is hydrogen, $C_1$-$C_{20}$ alkyl, or aryl.

In some embodiments, the compound has the following chemical structure:

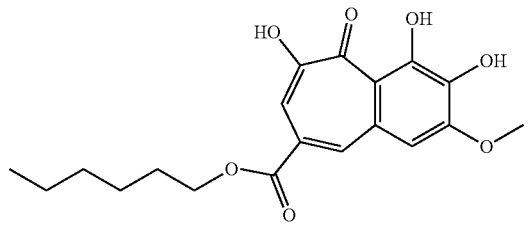 [SMILES: CCCCCCOC(=O)c1cc(O)c(=O)c2c(O)c(O)c(OC)cc2c1]

In some embodiments, the TLR4 inhibitory compound has the following chemical structure:

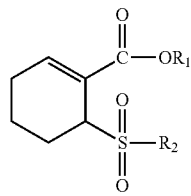

wherein:
$R_1$ is $C_1$-$C_{12}$ alkyl;
$R_2$ is $(CH_2)_n$—$R_3$, or N—$R_3R_4$;
$R_3$ is aryl or substituted aryl having at least one halogen substituent;
$R_4$ is hydrogen or $C_1$-$C_{12}$ alkyl, and
n is an integer from 1 to 4.

In some embodiments, the compound has the following chemical structure:

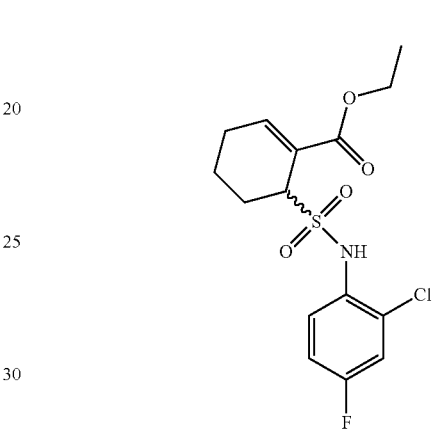

In some embodiments, the inactivation of the TLR2 and TLR4 genes in the cells is achieved by a peptide inhibitor of TLR2/TLR4 comprising the sequence PGFLRDPWCKY-QML (SEQ ID NO: 39).

In some embodiments, the inactivation of the TLR2 and TLR4 genes in the cells is achieved by a peptide inhibitor of TLR2/TLR4 comprising the sequence "DRQIKIWFQN-RRMKWKKPGFLRDPWCKYQML" (SEQ ID NO: 40).

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION

Figures 1A, 1B, 1C, 1D, 1E:
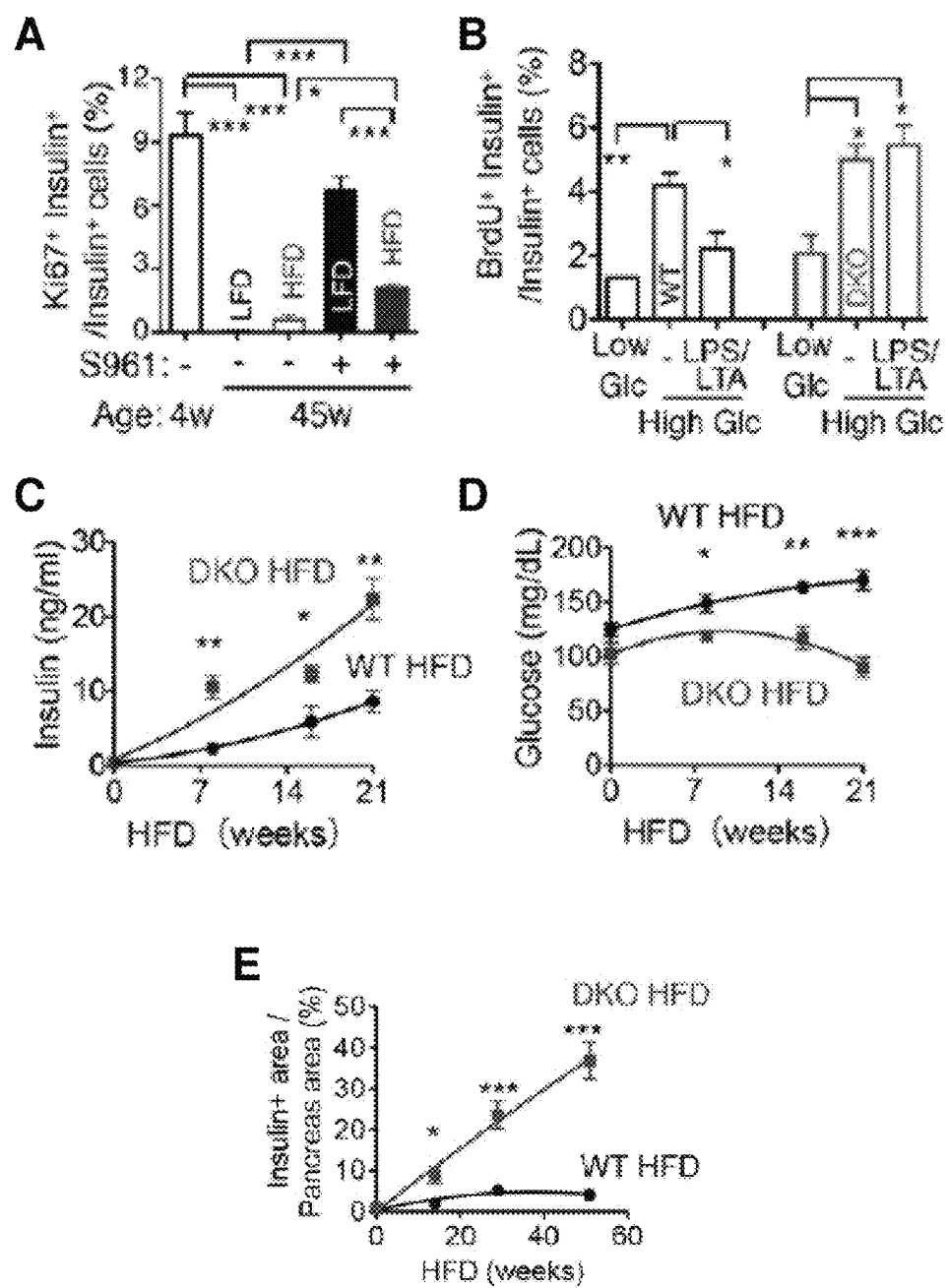
FIGS. 1A-1J. The loss of TLR2 and TLR4 leads to massive β cell expansion and improved glucose tolerance in a mouse model of diet-induced obesity. (A) Quantification of $Ki67^+$ β cells in WT mice at age of 4 or 45 weeks, either fed a LFD or 39-week HFD (starting at 6-weeks of age), with or without insulin receptor antagonist S961 for the last 2 weeks. (B) Flow cytometric analysis of $BrdU^+$ β cells in primary mouse islets cultured in 2.8 mM (low) or 22.8 mM (high) glucose, treated with or without LPS/LTA for 72 hr. (C-D) Serum insulin (C) and glucose (D) levels of WT and DKO mice at different time points during HFD feeding after a 5-hr fast. (E) Quantification of insulin-positive areas normalized to the total pancreas area is shown. (F) Pictures of pancreas from mice after 51 weeks of HFD feeding, highlighting visually visible islets in DKO mice (arrows). (G-H) Representative images of H&E (G) and insulin/glucagon (H) in pancreatic sections of mice after 51 weeks of HFD feeding. (I-J) 6 week-old mice were fed with either LFD or HFD for 14 weeks and analyzed for glucose tolerance test (I) and insulin tolerance test (J). Asterisks denote the statistical differences between the cohorts. a, n=3-5 mice each; b, n=9 mice pooled for each genotype, representative experiment shown from 3 repeats; c, n=6 or 8 mice with 2 repeats; d, n=4 or 6 mice each; e, n=3 or 4 mice each; f-h, representative data from 3 mice each; and i-j, n=12 mice each with 3 repeats. Values represent mean±SEM. *, p<0.05; , p<0.01; and *, p<0.001, using a one-way ANOVA with Newman-Keuls post-test (a-b) or two-tailed Student's t test (c-e and i-j)

In the following description, reference is made to the accompanying drawings that form a part hereof, and in which is shown by way of illustration specific embodiments which may be practiced. These embodiments are described in detail to enable those skilled in the art to practice the invention, and it is to be understood that other embodiments may be utilized and that logical changes may be made without departing from the scope of the present invention.

The following description of example embodiments is, therefore, not to be taken in a limited sense, and the scope of the present invention is defined by the appended claims.

The Abstract is provided to comply with 37 C.F.R. § 1.72(b) to allow the reader to quickly ascertain the nature and gist of the technical disclosure. The Abstract is submitted with the understanding that it will not be used to interpret or limit the scope or meaning of the claims.

Definitions

Unless defined otherwise, all technical and scientific terms used herein have the same meaning as commonly understood by one of ordinary skill in the art to which this invention belongs.

As used herein, the term "about" refers to an approximately +/−10% variation from a given value.

The term "allogeneic" refers to cells or tissues obtained from a different subject, typically a different subject of the same animal species.

The term "autologous" refers to cells or tissues obtained from a subject and used to treat that same subject.

As used herein, the term "CRISPR" refers to a caspase-based endonuclease comprising a caspase, such as Cas9, and a guide RNA that directs DNA cleavage of the caspase by hybridizing to a recognition site in the genomic DNA.

The term "diabetes" or "diabetes mellitus" as used herein refers to disease conditions in which the glucose metabolism is impaired, which results in hyperglycaemia. According to the World Health Organization (WHO), diabetes can be subdivided into four classes. Type 1 diabetes is caused by a lack of insulin. Insulin is produced by pancreatic islet cells. Pancreatic islet cells may be destroyed by an autoimmune reaction in Type 1 diabetes (T1D) (Type 1a). Moreover, Type 1 diabetes also encompasses an idiopathic variant (Type 1b or also known as diabetes of unknown origin). This form of Type 1 diabetes is not autoimmune in nature, and tests for islet cell antibodies will come up negative. Type 2 diabetes (T2D) is caused by an insulin resistance. Type 3 diabetes (T3D) comprises all other specific types of diabetes mellitus. For example, the beta cells may have genetic defects affecting insulin production, insulin resistance may be caused genetically, or the pancreas may be destroyed or impaired. Moreover, hormone deregulation (e.g. during pregnancy) or drugs may also cause Type 3 diabetes. Type 4 diabetes (T4D) is associated with older age rather than weight gain. Diabetes is diagnosed either by a plasma glucose level being higher than 110 mg/dl in the fasting state or being higher than 220 mg/dl after a meal. Symptoms of diabetes are well known in the art and are described in the publications by American Diabetes Association, e.g. "Diagnosis and classification of diabetes mellitus", *Diabetes Care,* 37.Supplement 1 (2014): S81-S90.

The term "DNA," as used herein, refers to a nucleic acid molecule of one or more nucleotides in length, wherein the nucleotide(s) are nucleotides. By "nucleotide" it is meant a naturally-occurring nucleotide, as well modified versions thereof. The term "DNA" includes double-stranded DNA, single-stranded DNA, isolated DNA such as cDNA, as well as modified DNA that differs from naturally-occurring DNA by the addition, deletion, substitution and/or alteration of one or more nucleotides as described herein.

As used herein, the term "effective amount" means the total amount of each active component of a pharmaceutical composition or method that is sufficient to show a meaningful patient benefit, i.e., treatment, healing, prevention of the relevant medical condition, amelioration of the symptoms, or an increase in rate of treatment, healing, prevention or amelioration of such conditions, or inhibition of the progression of the condition. When applied to an individual active ingredient, administered alone, the term refers to that ingredient alone. When applied to a combination, the term refers to combined amounts of the active ingredients that result in a desired therapeutic effect, whether administered in combination, serially or simultaneously.

The term "gene," as used herein, refers to a segment of nucleic acid that encodes an individual protein or RNA and can include both exons and introns together with associated regulatory regions such as promoters, operators, terminators, 5' untranslated regions, 3' untranslated regions, and the like.

As used herein, the term "nucleic acid" has its general meaning in the art and refers to refers to a coding or non coding nucleic sequence. Nucleic acids include DNA (deoxyribonucleic acid) and RNA (ribonucleic acid) nucleic acids. Examples of nucleic acid thus include but are not limited to DNA, mRNA, tRNA, rRNA, tmRNA, miRNA, piRNA, snoRNA, and snRNA. Nucleic acids thus encompass coding and non coding region of a genome (i.e. nuclear or mitochondrial).

The term "PDX-1" refers to the gene with the Entrez Gene number 3651, and also known as "Pancreatic and duodenal homeobox 1".

The term "small molecule compound" herein refers to small organic chemical compound, generally having a molecular weight of less than 2000 daltons, 1500 daltons, 1000 daltons, 800 daltons, or 600 daltons.

The term "subject" or "patient," as used herein, refers to a mammal who has or is suspected of having a disease or condition.

By "stem cell" is meant an undifferentiated cell that is capable of essentially unlimited propagation under appropriate conditions in vivo or ex vivo and is capable of differentiation to other cell types (e.g., a progenitor or precursor cell, such as a pancreatic precursor cell, or a fully differentiated cell, such as a pancreatic beta islet cell). Stem cells include, for example, embryonic stem cells and adult stem cells.

The term "TLR2" refers to the gene with the Entrez Gene number 7097, and also known as "Toll Like Receptor 2".

The term "TLR4" refers to the gene with the Entrez Gene number 7099, and also known as "Toll Like Receptor 4".

The terms "treating" or "treatment" refer to amelioration of a disease or disorder (i.e., arresting or reducing the development of the disease or at least one of the clinical symptoms thereof). In some embodiments, "treating" or "treatment" refers to ameliorating at least one disease symptom or physical parameter, which may or may not be discernible by the subject. In some embodiments, "treating" or "treatment" refers to modulating the disease or disorder, either physically, (e.g., stabilization of a discernible symptom), physiologically, (e.g., stabilization of a physical parameter), or both. In yet another embodiment, "treating" or "treatment" refers to delaying the onset of the disease or disorder, or even preventing the same.

General Description

It has been demonstrated herein that a combined action of Toll-like receptor 2 and Toll-like receptor 4 (TLR2/TLR4) plays a direct role in pancreatic β cell regeneration and hence increasing insulin production. In particular, it has been demonstrated herein that the loss of TLR2/TLR4, together but not individually, dramatically increases facultative β cell replication. Accordingly, the present invention is directed to treating diabetes by providing insulin-producing cells whose TLR2 and TLR4 genes have been inactivated.

Cells

Cells whose TLR2 and TLR4 genes are inactivated include insulin producing cells of a pancreatic tissue, and insulin-producing cells of a non-pancreatic origin.

In some embodiments, the cells are insulin producing cells of a pancreatic tissue, for example, cells of the islets, or β cells. According to these embodiments, cells of a pancreatic tissue, when provided to a recipient, can be in the form of isolated cells (e.g., β cells), islets, a pancreatic tissue containing islets, or a pancreas.

Methods of isolating pancreatic islet cells are known in the art (Field et al., *Transplantation*, (1996), 61:1554; Linetsky et al., *Diabetes*, (1997) 46:1120). Fresh pancreatic tissue can be divided by mincing, teasing, comminution and/or collagenase digestion. The islets are then isolated from contaminating cells and materials by washing, filtering, centrifuging or picking procedures. Methods and apparatus for isolating and purifying islet cells are described in U.S. Pat. Nos. 5,447,863, 5,322,790, 5,273,904, and 4,868,121. The isolated pancreatic cells may be cultured, using any suitable method of culturing islet cells as is known in the art. See e.g., U.S. Pat. No. 5,821,121.

In some embodiments, the pancreatic tissue can be autologous. In other embodiments, the pancreatic tissue can be allogeneic. Allogeneic cells can be supplied from a cell repository (such as a cell bank) or from an individual donor.

In some embodiments, cells of a pancreatic tissue are subjected to inactivation of the TLR2 and TLR4 genes ex vivo. In other embodiments, cells of a pancreatic tissue are subjected to inactivation of the TLR2 and TLR4 genes in vivo.

In some embodiments, cells whose TLR2 and TLR4 genes are inactivated are insulin producing cells of a non-pancreatic origin. Such cells include insulin-producing cells derived from cells of a non-pancreatic origin, e.g., stem cells, progenitor cells, or cells of non-pancreatic tissues.

As used herein, the term "stem cells" include totipotent, multipotent, or pluripotent stem cells. Stem cells suitable for use herein can be selected from the group consisting of pancreatic stem cells, adult stem cells, induced pluripotent stem cells (iPSCs), embryonic stem cells, umbilical cord blood cells, amnion cells, placenta cells, umbilical cord vein cells, umbilical cord matrix cells, a hematopoietic stem cell, hepatic stem cell, and progenitor-like stem cells. Directing differentiation of stem cells towards the pancreatic lineage is known in the art, as exampled by Van Hoof et al. (*Stem Cell Research* (2011) 6 (3): 276-285), Lumelsky et al. (*Science* (2001) 292 (5520): 1389-1394), and Ramiya et al. (*Nature Medicine* (2000) 6 (3): 278-282).

In some embodiments, insulin producing cells are derived from cells of a non-pancreatic tissue. Cells of a non-pancreatic tissue can be modified to function as a pancreatic islet cell, i.e., store, process and secrete pancreatic hormones, like insulin, upon an extracellular trigger, by inducing the expression of the PDX-1 gene in the cells, for example, as described in WO 2004/098646. Cells of a non-pancreatic tissue, which can be modified to function as a pancreatic islet cell, can be selected from cells of bone marrow, muscle, spleen, kidney, blood, skin, or liver. In one embodiment, the cell is a hepatocyte, i.e., a liver cell. In one embodiment, the cell is from a non-endocrine tissue.

Inactivation of the TLR2 and TLR4 genes in insulin-producing cells derived from cells of a non-pancreatic origin can be achieved in the cells of a non-pancreatic origin, from stem cells or cells of a non-pancreatic tissue, prior to directing differentiation of these cells into insulin-producing cells. Alternatively, inactivation of the TLR2 and TLR4 genes in insulin-producing cells derived from cells of a non-pancreatic origin can be achieved after differentiation of the cells of a non-pancreatic origin to insulin-producing cells have been completed.

In some embodiments, in addition to having the TLR2 and TLR4 genes inactivated, insulin-producing cells derived from cells of a non-pancreatic origin can also be engineered to have an induced PDX-1 expression. Inducing PDX-1 expression in cells has been shown in the art to induce pancreatic endocrine phenotype and function. Pancreatic phenotype can include production and secretion of pancreatic hormones in response to external stimuli (such as production and secretion of insulin in response to glucose), and/or storage of insulin. Methods and compositions that can be used to induce PDX-1 expression are described in the art, e.g. in WO2004/098646, and Meivar-Levy et al. (*The Israel Medical Association Journal: IMAJ* (2006), 8 (6): 430-434.) In some embodiments, inducing PDX-1 expression is achieved by introducing to a cell (a cell of a non-pancreatic origin, or an insulin-producing cell derived therefrom), a nucleic acid encoding and expressing a PDX-1 polypeptide.

Inactivation of TLR2 and TLR4

Inactivation of the TLR2 and TLR4 genes in insulin-producing cells provides one or more benefits. In one embodiment, inactivation of the TLR2 and TLR4 genes in pancreatic β cells can increase the volume of islets within the pancreatic tissue. In one embodiment, inactivation of the TLR2 and TLR4 genes in pancreatic β cells can increase the mass of β cells within the islets. In one embodiment, inactivation of the TLR2 and TLR4 genes in pancreatic β cells can increase the proliferation of pancreatic β cells. In one embodiment, inactivation of the TLR2 and TLR4 genes in pancreatic β cells can improve the ability of pancreatic β cells and islets to survive, e.g., to survive after an injury. The injury could result from a number of factors, such as, for example, from infection, disease, mechanical stress, hypoxia, chemical or pharmacological insults and the like. In one embodiment, inactivation of the TLR2 and TLR4 genes in pancreatic β cells or other insulin-producing cells increases the amount of insulin produced or secreted by the cells. In one embodiment, inactivation of the TLR2 and TLR4 genes in pancreatic β cells or other insulin-producing cells can increase the amount of insulin secreted by the cells in response to glucose.

Inactivation of the TLR2 and TLR4 genes in cells can be achieved, for example, by genetic inactivation or by utilizing inhibitory compounds.

Genetic Inactivation of TLR2 and TLR4

In some embodiments, inactivation of TLR2 or TLR4 includes a deletion of the whole or a part of the gene such that no functional protein product is expressed (also known as gene knock out). Inactivation of a gene may include a deletion of the promoter or the coding region, in whole or in part, such that no functional protein product is expressed. In other embodiments, inactivation of TLR2 or TLR4 includes introducing an inactivating mutation into the gene, such as an early STOP codon in the coding sequence of the gene, such that no functional protein product is expressed.

In some embodiments, gene inactivation is achieved using available gene targeting technologies in the art. Examples of gene targeting technologies include the Cre/Lox system (described in Kuhn, R., & M. Tones, R., *Transgenesis Techniques: Principles and Protocols*, (2002), 175-204.), homologous recombination (described in Capecchi, Mario R. *Science* (1989), 244: 1288-1292), and TALENs (described in Sommer et al., *Chromosome Research* (2015), 23: 43-55, and Cermak et al., *Nucleic Acids Research* (2011): gkr218.).

In one embodiment, TLR2 and TLR4 inactivation is achieved by a CRISPR/Cas system. CRISPR-Cas and similar gene targeting systems are well known in the art with reagents and protocols readily available (Mali, P. et al., (2013), *Science*, 339(6121), 823-826; Hsu, P. D. et al., (2014), *Cell*, 157.6: 1262-1278.). Exemplary genome editing protocols are described in Jennifer Doudna, and Prashant Mali, "*CRISPR-Cas: A Laboratory Manual*" (2016) (*CSHL Press*, ISBN: 978-1-621821-30-4) and Ran, F. Ann, et al. *Nature Protocols* (2013), 8 (11): 2281-2308.

A CRISPR endonuclease comprises two components: (1) a caspase effector nuclease, typically microbial Cas9; and (2) a short "guide RNA" (gRNA or sgRNA) comprising a ~20 nucleotide targeting sequence that directs the nuclease to a location of interest in the genome. When co-expressed with an artificial sgRNA targeting a cellular gene, the Cas9 endonuclease generates double-stranded breaks of DNA at the targeted locus. This method typically produces small insertions and deletions (indels) that shift the open reading frame (ORF) of the targeted gene and result in premature termination of translation and loss-of-function phenotypes.

In some embodiments, sgRNAs and Cas9 are cloned into plasmids and then introduced into mammalian cells by transfection. In some embodiments, sgRNAs and Cas9 are cloned into lentiviral vectors, packaged into viral particles, and transduced into target cells. Both the sgRNA and Cas9 are stably integrated into the host cell genome, and can be passed along to daughter cells when the cells divide. This provides for permanent expression of shRNA and Cas9, thus permanently knocking out target gene expression. In some embodiments, multiple sites in the genome are targeted by expressing multiple guide RNAs in the same cell, each having a different targeting sequence.

Inhibitory Compounds of TLR2 and TLR4 Signaling

In some embodiments, inactivation of TLR2 and TLR4 can be achieved by using compounds (e.g. small molecules) that inhibit TLR2 and TLR4 signaling pathways.

In some embodiments, blocking the signaling of TLR2 and TLR4 is achieved through using an oxidized phospholipid. In a some embodiments, the phospholipid has the following chemical structure:

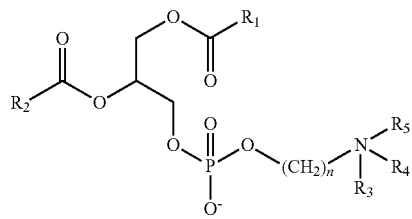

wherein:
$R_1$ is $C_{10}$-$C_{22}$ alkyl;
$R_2$ is $C_{10}$-$C_{22}$ alkenyl having 1-6 double bonds;
$R_3$, $R_4$ and $R_5$ are independently hydrogen or $C_1$-$C_{12}$ alkyl; and
n is an integer from 1-4.

In a specific embodiment, the phospholipid has the chemical name "1-palmitoyl-2-arachidonyl-snglycero-3-phosphorylcholine" (PAPC) and the following chemical structure:

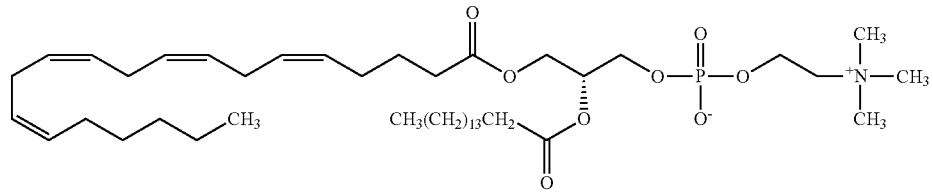

In particular embodiments of the present invention, the agent that inhibits signaling of both TLR2 and TLR4 is (oxy(1-palmitoyl-2-arachidonyl-snglycero-3-phosphorylcholine)) marketed under the brand name OxPAPC, which is a mixture of oxidized phospholipids with the following chemical structures:

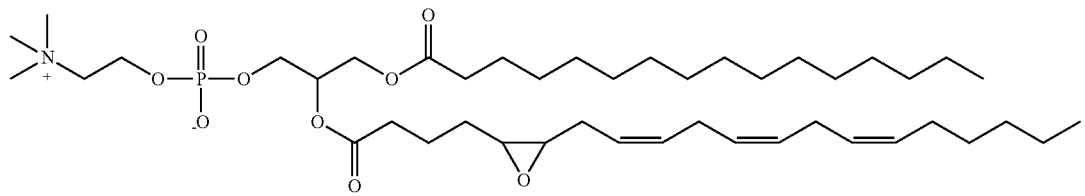

Chemical Formula: $C_{44}H_{80}NO_9P$
Molecular Weight: 798.08

-continued

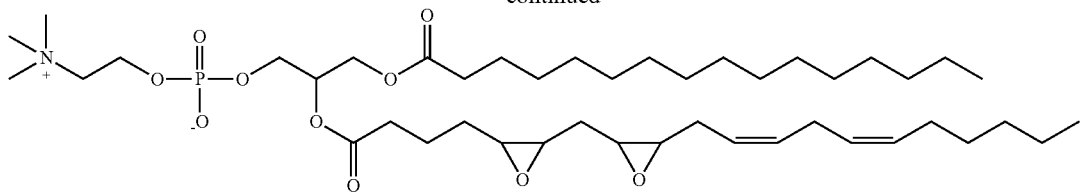

Chemical Formula: C$_{44}$H$_{80}$NO$_{19}$P
Molecular Weight: 814.08

+

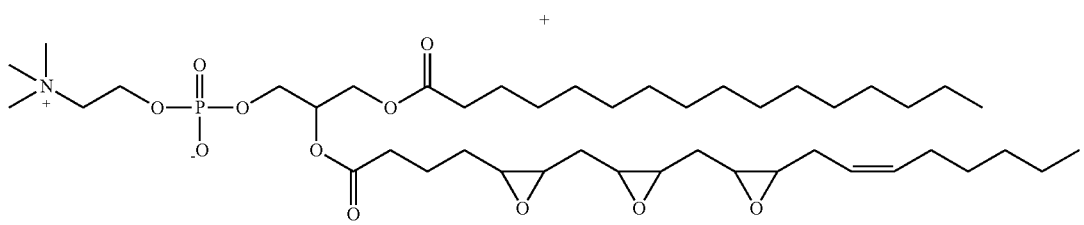

Chemical Formula: C$_{44}$H$_{80}$NO$_{11}$P
Molecular Weight: 830.08

+

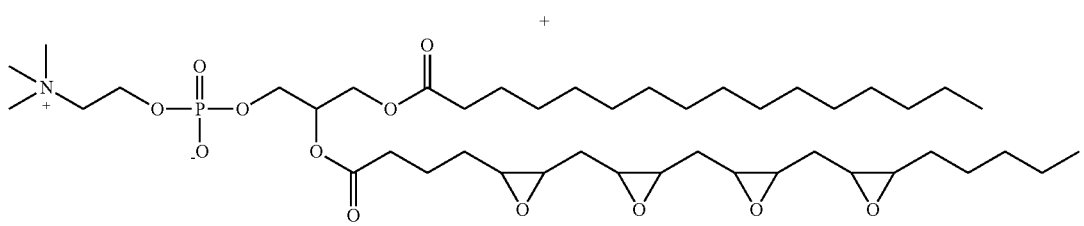

Chemical Formula: C$_{44}$H$_{80}$NO$_{12}$P
Molecular Weight: 846.08

In some embodiments, inactivation of TLR2 can be achieved with a small molecule TLR2 inhibitor, such as a small molecule TLR2 inhibitor described in U.S. Pat. No.: 9,517,993.

In some embodiments, the small molecule TLR2 inhibitor has the chemical structure:

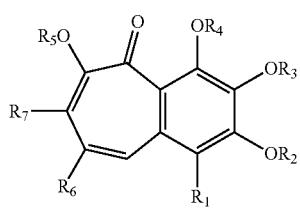

wherein:

R$_1$ and R$_7$ is hydrogen or C$_1$-C$_{12}$ alkyl;

R$_2$, R$_3$, R$_4$ and R$_5$ R$_5$are independently hydrogen, C$_1$-C$_{12}$ alkyl, or C$_3$-C$_{12}$ cyclocakyl;

R$_6$ is COOR$_8$, CONHR$_8$; and

R$_8$ is hydrogen, C$_1$-C$_{20}$ alkyl, or aryl.

In a specific embodiment, the TLR2 inhibitor has the chemical name "3,4,6-Trihydroxy-2-methoxy-5-oxo-5H-benzocycloheptene-8-carboxylic acid hexyl ester" and with the following chemical structure (also marketed under the brand name "CU CPT 22" by Sigma-Aldrich Co LLC):

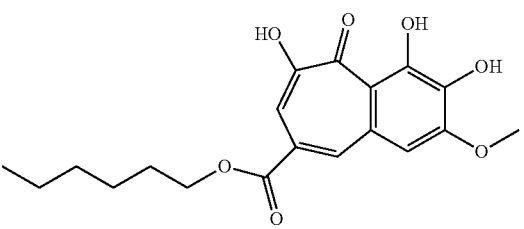 [SMILES: CCCCCCOC(=O)c1cc(O)c(=O)c2c(O)c(O)c(OC)cc2c1]

In some embodiments, inactivation of TLR4 can be achieved with a small molecule TLR4 inhibitor, such as a small molecule TLR4 inhibitor described in U.S. patent application Ser. No.: 12/227,359.

In some embodiments, the small molecule TLR4 inhibitor has the chemical structure:

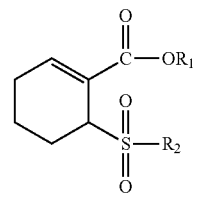

wherein:

R$_1$ is C$_{1-12}$ alkyl;

R$_2$ is (CH$_2$)$_n$—R$_3$, or N—R$_3$R$_4$;

R$_3$ is aryl or substituted aryl having at least one halogen substituent;

R$_4$ is hydrogen or C$_{1-12}$ alkyl, and n is an integer from 1 to 4.

In some embodiments, the TLR4 inhibitor is a small molecule having the chemical name "ethyl (6R)-6-[(2-chloro-4-fluorophenyl) sulfamoyl]cyclohexene-1-carboxylate" and the following chemical structure (also marketed under the brand name "CLI-095" or "TAK-242" by Invivogen):

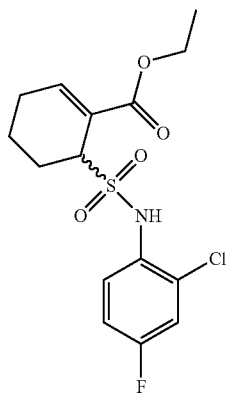 [SMILES: CCOC(=O)C1=CCCCC1S(=O)(=O)Nc1ccc(F)cc1Cl]

In some embodiments, pharmacological inhibition of TLR2 and TLR4 is achieved by using a combination of a TLR2 inhibitor and a TLR4 inhibitor.

In some embodiments, inactivation of TLR2/TLR4 can be achieved by using a peptide inhibitor of TLR2/TLR4 signaling. In one embodiment, the peptide inhibitor of TLR2/TLR4 signaling comprises the sequence "PGFLRDPWCKYQML" (SEQ ID NO: 39). In a specific embodiment, the peptide inhibitor of TLR2/TLR4 signaling comprises the sequence "DRQIKIWFQNRRMKWKKPGFLRDPWCKYQML" (SEQ ID NO: 40).

In some embodiments, the TLR2/TLR4 inhibition is achieved by specific neutralizing antibodies against TLR 2 and TLR4. In some specific embodiments, anti-hTLR2-IgA (Clone B4H2) (Invivogen, CA) or PAb-hTLR2 polyclonal antibody (Invivogen, CA) is used to inhibit TLR2. In other embodiments, anti-hTLR4-IgG (Clone W7C11) (Invivogen, CA) or PAb-hTLR4 polyclonal antibody (Invivogen, CA) is used to inhibit TLR4.

Treatment

In one aspect, the present method treats diabetes in a subject, by providing insulin-producing cells, wherein the TLR2 and TLR4 genes in the cells have been inactivated. In some embodiments, the subject is a type-1 or type-2 diabetic patient.

In some embodiments, the method includes obtaining insulin-producing cells whose TLR2 and TLR4 genes have been inactivated, and transplanting such cells to a subject having diabetes.

In some embodiments, the method includes obtaining insulin-producing cells from a subject, treating these cells ex vivo to inactivate the TLR2 and TLR4 genes (through genetic inactivation or use of an inhibitor compound). The cells whose TLR2 and TLR4 genes have been inactivated can be subsequently used in transplantation into a diabetic subject, e.g., a subject having T1D or T2D. The subject can be a donor of the cells that are treated ex vivo and used in the transplantation.

Transplant patients typically receive two infusions with an average of 50,000 to 100,000 islets per transplantation under the kidney capsules. Once implanted, cells capable of producing insulin begin to make and release insulin.

In some embodiments where transplanted cells are allogeneic, transplantation involves immunosuppression of the patient to prevent host rejection of the donor cells. In alternative embodiments, cells are encapsulated before transplantation. Encapsulation methods and materials are known in the art (described in Sakata et al., *World J Gastrointest Pathophysiol.* (2012); 3(1): 19-26, and U.S. Pat. No. 6,365,385; incorporated herein by reference).

In some embodiments, cells capable of producing insulin and/or regenerating β cells within a subject are treated in vivo to inactivate the TLR2 and TLR4 genes. In vivo treatment of cells can be achieved by delivery of suitable agents (e.g., agents for gene editing (CRISPR, TALEN etc.), or inhibitory compounds) through various means such as local injection (i.e., injection into the transplanted cells or recipient tissue or organ), viral delivery (as described in Giacca, Mauro, and Serena Zacchigna, (2012), *Journal of Controlled Release*, 161.2 (2012): 377-388.), or nanoparticle-mediated delivery (as described in Jin, Sha, and Kaiming Ye., (2007), *Biotechnology Progress*, 23.1: 32-41).

Unless defined otherwise, all technical and scientific terms used herein have the same meaning as commonly understood by one skilled in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

The specific examples listed below are only illustrative and by no means limiting.

EXAMPLES

Example 1

Materials and Methods

Mice.

Tlr2/Tlr4 DKO mice on the C57BL/6 background have been previously described (R. P. Darveau et al., *Infect Immun*, 72, 5041-5051 (2004); Y. Ji et al., *Cell Reports*, 8, 137-149 (2014)). WT C57BL/6, Tlr2-/-(B6.129-Tlr2$^{tm1Kir}$/J), and Tlr4-/-(B6.B10ScN-Tlr4$^{lps-del}$/JthJ) mice were purchased from the Jackson Laboratory (#000664, #004650 and #007227, respectively). All mice were bred, reared, and housed in our specific pathogen-free facility. Mice were fed a low-fat diet (LFD) composed of 13% fat, 67% carbohydrate, and 20% protein from Harlan Teklad (#2914), or a highfat diet (HFD), starting at 6 weeks of age, composed of 60% fat, 20% carbohydrate, and 20% protein from Research Diets Inc. (D12492) for up to a year. The fatty acid composition of these diets has been described previously (Y. Ji et al., *J Biol Chem*, 287, 13561-13571 (2012)). All animals were sacrificed by cervical dislocation and tissues were immediately harvested. Frozen tissues were stored at −80° C. All animal procedures were approved by and done in accordance with the Cornell IACUC (#2007-0051) and University of Michigan Medical School (#PRO00006888).

Power analysis of the animal size: Based on sample size formula of the power analysis, $N=8(CV)^2[1+(1-PC)^2]/(PC)^2$, to reach the error=0.05, Power=0.80, percentage change in means (PC)=20%, co-efficient of variation (CV)=10~15% (varies between the experiments), 4-6 mice per group are the minimal number of mice to obtain statistical significance. Together with our prior experience, we routinely used a total of 4-6 mice in each study to ensure adequate power. Mice in each group were randomly chosen based on the age, genotype and gender.

Human Studies (a) Donor info for Q-PCR analysis of TLR expression in islets from Joslin (R.K.):

| Gender: | Ethnicity/Race | Age | BMI | Diabetic donor status |
|---|---|---|---|---|
| Male: | Hispanic/Latino | 49 | 31.3 | Non-DM |
| Female: | White | 52 | 31.4 | Non-DM |
| Female: | Hispanic/Latino | 24 | 19.5 | Non-DM |
| Male: | Hispanic/Latino | 58 | 31.2 | Non-MD |
| Female: | White | 36 | 42.7 | Non-DM |
| Male: | Caucasian | 49 | 28.2 | T2D |
| Male: | Unknown | 53 | 31.0 | T2D |
| Male: | Caucasian | 48 | 35.8 | T2D |
| Male: | Asian | 49 | 23.9 | T2D |
| Male: | Asian | 49 | 23.9 | T2D |

Total RNA was extracted using RNeasy Kit (Qiagen). cDNAs were synthesized using a High-Capacity cDNA RT Kit (ABI). Q-PCR analysis of TLR expression was performed with SYBR Green (Bio-Rad) using ABI 7900HT.

(b) Donor info for flow cytometric analysis of proliferation in islets from the Integrated Islet Distribution Program (IIDP) at UPENN (C.L. and A.N.):

| Gender: | Ethnicity/Race | Age | BMI | Diabetic donor status |
|---|---|---|---|---|
| Female (Donor 1): | Hispanic | 24 | 32.2 | Non-DM |
| Male (Donor 2): | Caucasian | 46 | 19.13 | Non-DM |
| Male (Donor 3): | Caucasian | 47 | 32.2 | T2D |

High quality islet preparation with over 80-90 percent of viability was sent to the Qi laboratory at the University of Michigan Medical School. Upon arrival, islets were treated as described below.

Drug Treatment In Vivo

For S961 studies, 45-week-old mice under a LFD or HFD were anesthetized and subcutaneously implanted with osmotic pumps (ALZET) filled with insulin receptor antagonist S961 4 or vehicle PBS. Mice were infused with S961 at the dose of 10 nmoles/week for 2 weeks, followed by euthanization and histological analysis of islets. For MEK162 studies, TLR2/TLR4 DKO mice on HFD for 8 weeks were orally gavaged with MEK162 (20 mg/kg body weight, LC laboratories) or vehicle, twice daily for 2 days, followed by euthanization and histological analysis.

Bone Marrow Transplantation (BMT)

BMT was carried out as previously described (Sun, S. et al., Diabetes, 61, 1471-1478(2012)). Briefly, 6-week-old recipient male mice were sub-lethally irradiated (10 Gy) and transplanted i.v. with $5 \times 10^6$ bone marrow cells. Two weeks before irradiation, mice were treated with water containing 0.2 mg/ml ciprofloxacin and 1 mg/ml metronidazole and maintained for a total of 3 weeks. After a 6-week recovery on LFD feeding, chimeras were placed on HFD for 26 weeks.

Islet Transplantation Under the Kidney Capsule of Diabetic Mice

Islet kidney transplantation was performed as described previously (G. L. Szot et al., Journal of visualized experiments, JoVE, 404, (2007); E. J. Zmuda et al., Journal of visualized experiments, JoVE, (2011)). Recipient WT or DKO mice at the age of 6-10 weeks were injected with a single high-dosage of streptozotocin (STZ, Sigma) at 150 mg/kg body weight. Mice with non-fasted blood glucose higher than 300 mg/dl were defined diabetic and used as recipients. On the day of surgery, mice were anesthetized by isoflurane inhalation. After preparation of surgical-area skin, a 2 cm incision was made through the dermis right above the kidney. A small incision was further made on the peritoneal wall to expose the kidney. Using the 27-gauge needle, a small nick was made on the kidney capsule. Collected islets were in advance transferred and sedimented in a flexible PE50 tubing. The beveled end of the islets-containing PE50 tubing was carefully placed under the capsule, and the tubing was moved around gently to make a small pouch under kidney capsule. Islets were slowly delivered from the tubing into the subscapular pouch by gentle depressing the plunger of a 25 µl Hamilton syringe that was connected to the other end of the tubing. 100 primary islets isolated from donor WT and DKO mice were implanted under the capsule of either left or right kidney of the recipient. The nick on the kidney was cauterized with low heat. The kidney was placed back into the cavity and the peritoneum and skin were sutured. Ketoprofen were given preemptively (20-30 min prior to surgery) at the rate of 2.5-5 mg/kg subcutaneously and were continued once daily for next 2-3 days. After a 4-week recovery, mice were given HFD for 14 weeks, and kidneys were collected for histological analysis after euthanization.

Parabiosis

Parabiosis was performed as previously described (P. Kamran et al., Journal of visualized experiments JoVE, (2013)). Female mice in the same cage were anesthetized using an isoflurane vaporizer. Thoroughly shave the left side of the mouse placed on the left and the right side of the mouse placed on the right, starting at 1 cm above the elbow to 1 cm below the knee. Longitudinal skin incisions to the shaved sides of each animal were performed. Then the skin was gently detached from the subcutaneous fascia to create 0.5 cm of free skin along the entire incision. Then the mice were jointed by attaching the left olecranon of one animal to the right olecranon of the other. Then the knee joints were connected using the same procedure. After that, the skin of the two animals was connected with a continuous suture starting ventrally from the elbow towards the knee. Placed the mice in the prone position and continued the suture dorsally. Three weeks after surgery, the mice were given HFD and monitored for body weight and blood glucose levels. The mice were sacrificed after 14-weeks feeding of HFD for histological examination of the pancreas.

Primary Islet Purification

The duodenal opening of the bile ducts were clamped with a hemostat, and the bile ducts were cannulated and perfused with 2 ml Liberase TL Research Grade (0.3 mg/ml, Roche) in RPMI 1640 medium (Invitrogen). The expanded pancreases were removed and digested at 37° C. for 30 min, after which the reaction was stopped by addition of 20 ml of cold RPMI1640 medium containing 10% serum (FISHER). Digested pancreases were dissociated by vigorous shaking. After two washes in RPMI1640 medium, the digested tissues were filtered through a 450 µm nylon mesh suspended in a Histopaque 1077 (Sigma)/RPMI1640 medium gradient and centrifuged at 2400 RPM for 20 min. The islets were collected from the interface between the medium and Histopaque and resuspended in RPMI1640 medium containing 10% serum. Islets were washed three times and handpicked under a light microscope. The islets were cultured overnight in RPMI1640 medium containing 10% serum for analyses.

Human Islets

Human islets were received from the accredited Human Islet Resource Center at the University of Pennsylvania. The pancreata were obtained from the donors through the local organ procurement organization. The islets were isolated following the guidelines of Clinical Islet Transplantation (CIT) consortium protocol (Ricordi, C. et al., *Diabetes*, 65, 3418-3428 (2016)). Briefly, the pancreas was digested following intraductal injection of Collagenase & Neutral Protease (Serva) in Hanks' balanced salt solution. Liberated islets were then purified on continuous density gradients (Cellgro/Mediatech) using the COBE 2991 centrifuge and cultured in CIT culture media and kept in a humidified 5% $CO_2$ incubator.

Image Quantitation

For quantification of β cell area, six independent pancreatic tissue sections from 3-4 mice were randomly selected. Total insulin-positive and total pancreas area was measured using the Aperio Imagescope and ImageJ, from which percentage of insulin-positive area was calculated. For quantitation of β cell proliferation, cytoplasmic insulin and nuclear Ki67 double-positive cells were counted as proliferating β cells. Percent of proliferating cells were calculated by dividing the number of Ki67 and insulin-double positive cells by insulin-positive cells of each islet. Islets from 3-4 mice in each group with ~200-400 β cells in LFD and ~2,000-7,300 β cells in HFD cohorts were analyzed using the ImageJ software.

Glucose and Insulin Tolerance Tests

For glucose tolerance test (GTT), mice were fasted for 16-18 h followed by injection of glucose (Sigma) at 1 g/kg body weight. For insulin tolerance test (ITT), mice were fasted for 4-6 h followed by injection of insulin (Sigma) at 40m/kg body weight. Blood glucose was monitored using TRUEresult Glucometer (Nipro Diagnostics) at indicated time points.

Immunohistochemistry Staining

Pancreas was fixed in 4% paraformaldehyde, embedded in paraffin, and sectioned by Cornell Histology Core Facility. Ten-micrometer-thick paraffin sections were stained with hematoxylin/eosin. For staining of insulin with immunofluorescence, paraffinembedded sections were rehydrated by sequentially washing in xylene, 100%, 95%, 75% ethanol and water. Then slides were boiled in 1 mm EDTA for antigen exposure. After blocking using 5% donkey serum, primary guinea pig anti-rat insulin antibody (Linco, 1:200) were applied and incubated overnight at 4° C., followed with washes and incubation with FITC-conjugated donkey anti-guinea pig IgG (Jackson ImmunoResearch, 1:200). Slides were washed twice with water, applied with antifade/DAPI and covered with coverslips. Fluorescence Images were captured under a Zeiss LSM710 confocal microscope at Cornell Biotechnology Resource Center Imaging Facility. For horseradish peroxidase enzyme (HRP) staining, slides were stained with Histostain kit and DAB substrate from Invitrogen. Other primary antibodies used include: Insulin (1:200, Cell Signaling), Glucagon (1:1000, Sigma), Ki-67 (1:50, Abcam), PCNA (1:100, Santa Cruz), CD31 (1:100, Santa Cruz), PDX1 (1:100, Cell Signaling), and Ccnd2 (1:100, Santa Cruz). H&E and IHC sections were scanned using the Aperio Scanscope and pictures were taken at various magnifications. For horseradish peroxidase enzyme (HRP) staining, slides were stained with Histostain kit and DAB substrate from Invitrogen.

Flow Cytometry

Flow cytometric analysis of peripheral blood cells in mice of parabiosis experiment was performed as we previously described (Y. Ji et al., *Cell Reports*, 8, 137-149 (2014); Y. Ji et al., *J Biol Chem*, 287, 24378-24386 (2012)). The RBCs in the blood was lysed and resuspended in cold PBS with 5% FBS and 1% penicillin/streptomycin. The cell suspension were stained with either 1:100 or 1:200 fluorochrome- or biotin conjugated antibodies against CD4 (GK1.5), CD8 (YTS169), CD45 (30-F11), CD19 (6D5), avidin-PerCP or isotype control antibodies (BioLegend or BD Biosciences). The samples were analyzed by BD LSR cell analyzer at the Flow Cytometry Core Facility at Cornell University and the data were analyzed using the CellQuest software (BD Biosciences) and Flowjo (FlowJo LLC.)

Flow Cytometric Analysis of β Cell Proliferation and Senescence

Mouse and human islets were dissociated with Trypsin-EDTA (Thermofisher, 0.5%) and cultured in 96 well plate with RPMI 1640 medium containing 2.8 mM (low glucose) or 23 mM glucose (high glucose), with or without 20 μg/ml LPS and 2 μg/ml LTA, for 72 hr. Medium was changed every 24 hr. BrdU (10 μM) was added for the last 48 hr. Cells were collected and fixed in 4% PFA at 4° C. for 15 min. The samples were permeabilized with a BD Cytofix/Cytoperm fixation/permeabilization kit according to the manufacturer's protocol, followed by digestion with DNase I (Roche, 50 U/ml in 4.2 mM $MgCl2$ and 150 mM NaCl) at room temperature for 30 min. The rest of the procedures were performed as the regular flow cytometric analysis using anti-BrdU-PE (PRB-1, BD Biosciences) and anti-insulin antibody (Abcam). For analysis of p16INK4a expression, permeabilized cells were stained with anti-insulin and anti-p16 antibody (Santa Cruz 377412, 1:100). For analysis of cell senescence, dissociated β cells were cultured in RPMI 1640 medium containing 33 μM C12FDG (ThermoFisher) at 37° C. for 1 hour. Samples were analyzed using BD LSR cell analyzer at the Vision Research Core Facility at the University of Michigan Medical School. Data were analyzed using the CellQuest software (BD Biosciences) and Flowjo (FlowJo LLC.).

Quantitation of Immune Cells in Adipose Tissue

Single-cell suspension from stromal vascular cells (SVC) of adipose tissue was prepared as described (S. Xia et al., *J Biol Chem*, 286, 23591-23599 (2011)). SVCs from two fat pads per mouse were resuspended in PBS and $1×10^6$ cells were used for subsequent staining. Cells were first incubated with anti-CD16/CD32 antibody to block Fc receptors, and then incubated with antibodies for specific cell surface markers diluted at optimal concentrations for 20 min at 4° C. Cells were washed three times and then resuspended in PBS for analysis using the FACSCalibur Flow Cytometer (BD Biosciences). NKT cells were identified as CD45+ αGalCer-loaded CD1d-tetramer$^+$ CD3/TCRβ$^+$ lymphocytes; CD4$^+$ T cells were identified as CD4$^+$CD45$^+$ cells; CD8$^+$ T cells were identified as CD8$^+$ CD45$^+$ cells. αGalCer-loaded CD1d-tetramer-PE was provided by the NIH Tetramer Facility. Antibodies against CD3 (17A2) and TCRβ (H57-597) were from Biolegend.

Insulin and Multiplex ELISA Analyses

Serum insulin levels were measured following a 4 hour fast using ultrasensitive mouse/rat insulin ELISA kit (Crystal Chem) per supplier's instruction. For multiplex analysis, serum samples were collected from indicated mouse cohorts following a 4 hour fast and levels of various hormones were analyzed by Bio-Plex Pro™ Mouse Diabetes Panel 8-Plex (Cat. #171-F7001M) per manufacture's instruction. The use of the trademark Bio-Plex Pro™ refers to magnetic bead— based assays, available as either premixed panels or single-plex sets that rapidly detect multiple diabetes and obesity biomarkers in a single experiment, available commercially through BioRad Laboratories Inc.

In Vitro Islet Treatment

Islets were cultured in RPMI 1640 culture medium (10% FCS, 10 mM HEPES, 1 mM sodium pyruvate and 50 µM β-mercaptoethanol) overnight after isolation. Islets were then stimulated with either a combination of LPS (Sigma, 5 µg/ml) and lipoteichoic acid (LTA, Sigma, 1 m/ml), or a combination of 0.5 mM palmitic acid (PA, Sigma) and 22.2 mM glucose, for 24 hours. Islets were snap-frozen for mRNA and protein extraction.

Transmission Electron Microscopy (TEM)

Pancreatic tissues were collected from mice after 51 weeks of HFD feeding and immediately sliced into 1- to 2-mm$^3$ pieces and fixed, stained, dehydrated, and embedded in Poly/bed 812 (Polysciences). Embedded samples were cut with Leica Ultracut Ultramicrotome system and images were taken using JEM-1400 TEM on a fee-forservice basis at the Electron Microscopy and Histology Core Facility at Weill Cornell Medical College.

Islet Imaging and Perifusion

All imaging and perifusion experiments were conducted according to previously described methods (Adewola, A. F. et al., *Biomed Microdevices*, 12, 409-417 (2010); Xing, Y. et al., *Biomed Microdevices*, 18, 80 (2016)). In brief, islets were incubated in Krebs Ringer buffer (KRB) containing 2 mM glucose, 5 µM Fura-2/AM (Molecular Probes, CA) and 2.5 µM Rhodamine 123 (Sigma, MO) for 30 mins. The islets were then loaded into the temperature equilibrated microfluidic device mounted on an inverted epifluorescence microscope (Leica DMI 4000B, location). The KRB containing 14 mM glucose (20 min) or 30 mM KCl (15 min) was then administered to the islets. Dual-wavelength Fura-2/AM was excited at 340 and 380 nm and fluorescent emission was detected at 510 nm. These images were collected with a CCD (Retiga-SRV, Fast 1394, QImaging). Simple PCI software (Hamamatsu Corp. location) was used for image acquisition and analysis. Intracellular Ca2+ was expressed as a ratio of fluorescent emission intensity F340/F38. All fluorescence signals were expressed as "change-in-percentage" after being normalized against basal intensity levels established before stimulation. Perifusate samples were collected every 2 mins at the outlet at flow rate of 250 µl/min for insulin analysis using Mercodia Rodent Insulin ELISA kit (Uppsala, Sweden).

INS-1 Cell Line

Rat β cell line Ins-1 cells were obtained from Thermo-Fisher and authenticated by morphology, insulin expression and insulin secretion. Cells were cultured in RPMI 1640 culture medium (10% FCS, 10 mM HEPES, 1 mM sodium pyruvate). Cells were treated with MEK162 or vehicle for 1 hr and snap-frozen for protein extraction.

Preparation of Primary Macrophages

Peritoneal macrophages were obtained 4 days after intraperitoneal injection of 2 ml aged 4% brewed thioglycollate broth (VWR 90000-294). Mice were euthanized and macrophages were collected by injection of PBS into the peritoneal cavity and flush. The peritoneal exudate cells were centrifuged at ~1,000 rpm for 10 min and treated with red blood cells lyses buffer. Macrophages were suspended in culture medium and plated in 6-well plate. Macrophages were then cultured in medium containing 2.8 mM glucose (Low Glucose), 23 mM glucose (High Glucose), or stimulated with a combination of LPS (200 ng/ml) and lipoteichoic acid (LTA, 1 µg/ml) in 23 mM glucose medium, for 24 hr. Cells were snap-frozen for protein extraction.

Western Blot and Antibodies

Preparation of whole cell lysates and Western blots were performed as previously described (Sun, S. et al., *Nat Cell Biol*, 17, 1546-1555 (2015)). Phosphatase Inhibitor (LC laboratories) was added to prevent dephosphorylation when detecting phosphorylated proteins. Antibodies used in this study were: HSP90 (H-114, 1:6,000) and JNK1/2 (sc-571, 1:2,000) from Santa Cruz; p-Thr202/Tyr204 ERK1/2 (4370, 1:2,000), ERK1/2 (9102, 1:2,000), p-Ser217/221 MEK1/2 (9121, 1:1,000), MEK1/2 (4694, 1:1,000), p-Thr183/Tyr185 JNK1/2 (9255S, 1:2,000,), p-Ser473 AKT (9271S, 1:2,000), AKT (9272, 1:2,000), IκBα (9242, 1:2,000), p-Ser536 NFκB p65 (3033, 1:1,000), p-Thr172 AMPKα (2535, 1:2,000) and AMPKα (2532, 1:2,000) from Cell Signaling. Band density was quantitated using the Image Lab software on the ChemiDOC XRS+ system (Bio-Rad). Protein levels were normalized to HSP90 and the phosphorylated forms were normalized to phosphorylation-independent levels of the same protein. Data are presented as mean±SEM unless otherwise specified.

RNA Extraction, Reverse Transcription and Quantitative PCR (Q-PCR)

RNA extraction from cells and animal tissues, reverse transcription and Q-PCR analyses were performed as previously described (Xiao, X. et al., *J Clin Invest*, 123, 2207-2217 (2013)). Q-PCR data was collected with the Roche LightCycler 480 and was normalized to ribosomal 132 gene in each sample.

Primers

Q-PCR primers used for mouse genes:

```
Tnfa
(TCAGCCGATTTGCTATCTCATA (SEQ ID NO: 1),
AGTACTTGGGCAGATTGACCTC (SEQ ID NO: 2)), L32
(GAGCAACAAGAAAACCAAGCA (SEQ ID NO: 3);
TGCACACAAGCCATCTACTCA (SEQ ID NO: 4)), Casp1
(AGATGCCCACTGCTGATAGG (SEQ ID NO: 5),
TTGGCACGATTCTCAGCATA (SEQ ID NO: 6)), Reg1
(CATCCTGCTCTCATGCCTGAT (SEQ ID NO: 7),
GCAGATGGCAGGTCTTCTTCA (SEQ ID NO: 8))

Reg2
(TTTTGCCAGAACATGAATGC (SEQ ID NO: 9),
GTGCCAACGACGGTTACTTT (SEQ ID NO: 10))

Reg3b
(GGCTTCATTCTTGTCCTCCA (SEQ ID NO: 11),
AGATGGGTTCCTCTCCCAGT (SEQ ID NO: 12))

Reg3d
(GTGTTGCCTGATGTCCCTTT (SEQ ID NO: 13),
TTAGCCCAGGTCTGTGGTTC (SEQ ID NO: 14))

Mip1a
(TTCTCTGTACCATGACACTCTGC (SEQ ID NO: 15),
CGTGGAATCTTCCGGCTGTAG (SEQ ID NO: 16)),

Cxcl10
(AATCCGGAATCTAAGACCATCA (SEQ ID NO: 17),
GCAATTAGGACTAGCCATCCAC (SEQ ID NO: 18))

Chi3l3
(GGCTCAAGGACAACAATTTAGG (SEQ ID NO: 19),
ACTGTGGAAAAACCGTTGAACT (SEQ ID NO: 20))

Retn1a
(TATGAACAGATGGGCCTCCT (SEQ ID NO: 21),
AGCTGGGTTCTCCACCTCTT (SEQ ID NO: 22))
```

```
Ccl5
(GGAGTATTTCTACACCAGCAGCA (SEQ ID NO: 23),
ACAGGGAAGCTATACAGGGTCA (SEQ ID NO: 24))

IL1rn
(TTGTGCCAAGTCTGGAGATG (SEQ ID NO: 25),
TTCTCAGAGCGGATGAAGGT (SEQ ID NO: 26))

Clec7a
(TCATTGAAAGCCAAACATCG (SEQ ID NO: 27),
CCTGGGGAGCTGTATTTCTG (SEQ ID NO: 28))

Arg1
(CTCCAAGCCAAAGTCCTTAGAG (SEQ ID NO: 29),
AGGAGCTGTCATTAGGGACATC (SEQ ID NO: 30))
```

The Q-PCR conditions were: 94° C. for 5 min, 94° C. for 1 min, 58° C. for 20 sec and 72° C. for 30 sec repeated for 25 to 30 cycles according to individual template, followed by 70° C. for 10 min.

Q-PCR primers used for mouse and human genes:

```
hTlr2
(TGATGCTGCCATTCTCATTC (SEQ ID NO: 31),
CGCAGCTCTCAGATTTACCC (SEQ ID NO: 32))

hTlr4
(GGAGGAAGGGAGAAATGAGG (SEQ ID NO: 33),
CACCTCCAAAAGCTTCCTTG (SEQ ID NO: 34))

mTlr2
(GCTGGAGGACTCCTAGGCT (SEQ ID NO: 35),
GTCAGAAGGAAACAGTCCGC (SEQ ID NO: 36))

mTlr4
(ACCAGGAAGCTTGAATCCCT (SEQ ID NO: 37),
TCCAGCCACTGAAGTTCTGA (SEQ ID NO: 38))
```

The Q-PCR conditions were: 94° C. for 5 min, [94° C. for 15 sec, 58° C. for 15 sec and 72° C. for 30 sec] (40 cycles), followed by dissociation curve analysis.

Microarray

Islets were collected from mice on a HFD for 5 weeks or 7 months and snap-frozen in liquid nitrogen. RNA was extracted as described above. RNA quality and concentration were determined using the RNA 6000 Nano kit on an Agilent 2100 bioanalyser. The cDNA microarray of islets RNA was performed as previously described (S. Sun et al., *Nat Cell Biol*, 17, 1546-1555 (2015)).

Statistical Analysis.

Results were expressed as mean±SEM. Comparisons between groups were made by unpaired two-tailed Student's t test (two groups) and one-way ANOVA with Newman-Keuls post test (multiple groups). All experiments were repeated at least twice or performed with independent samples.

Example 2

The Loss of TLR2 and TLR4 Leads to Massive β Cell Expansion and Improved Glucose Tolerance in a Mouse Model of Diet-Induced Obesity The inventors discovered that β cell replication declined dramatically by nearly 100-fold from neonates to adult mice (FIG. 1A). In mouse models of diet-induced obesity and T2D, chronic feeding with HFD, which increased body weight and circulating glucose levels, elevated serum insulin level and triggered a modest increase of β cell replication and expansion with time (FIG. 1A). When challenged with insulin receptor antagonist S961 (Vikram, A. et al., *Biochem Biophys Res Commun*, 398, 260-265 (2010)), β cell replication in HFD mice was significantly augmented by 4-fold more than that with HFD feeding alone (FIG. 1A). However, the effect of S961 on β cell replication was still considerably lower on animals fed on HFD compared to those on LFD (2.0% in HFD+5961 vs. 6.7% in LFD+5961, $p<0.001$, (FIG. 1A). These findings point to the existence of a negative regulatory mechanism(s) that counter β cell replicative potential under HFD. It was also observed that TLR2- and TLR4-specific agonists lipoteichoic acid (LTA) and lipopolysaccharides (LPS) significantly suppressed hyperglycemia-induced β cell proliferation in islets in a TLR2- and TLR4-dependent manner (FIG. 1B). These findings point to a role of TLR2 and TLR4 in β cell proliferation in vivo.

Example 3

Mice with Combined Tlr2 and Tlr4 Deficiency (Double Knock-Out, DKO) Fed a High Fat Diet (HFD)

Figures 1F, 1G, 1H, 1I, 1J:
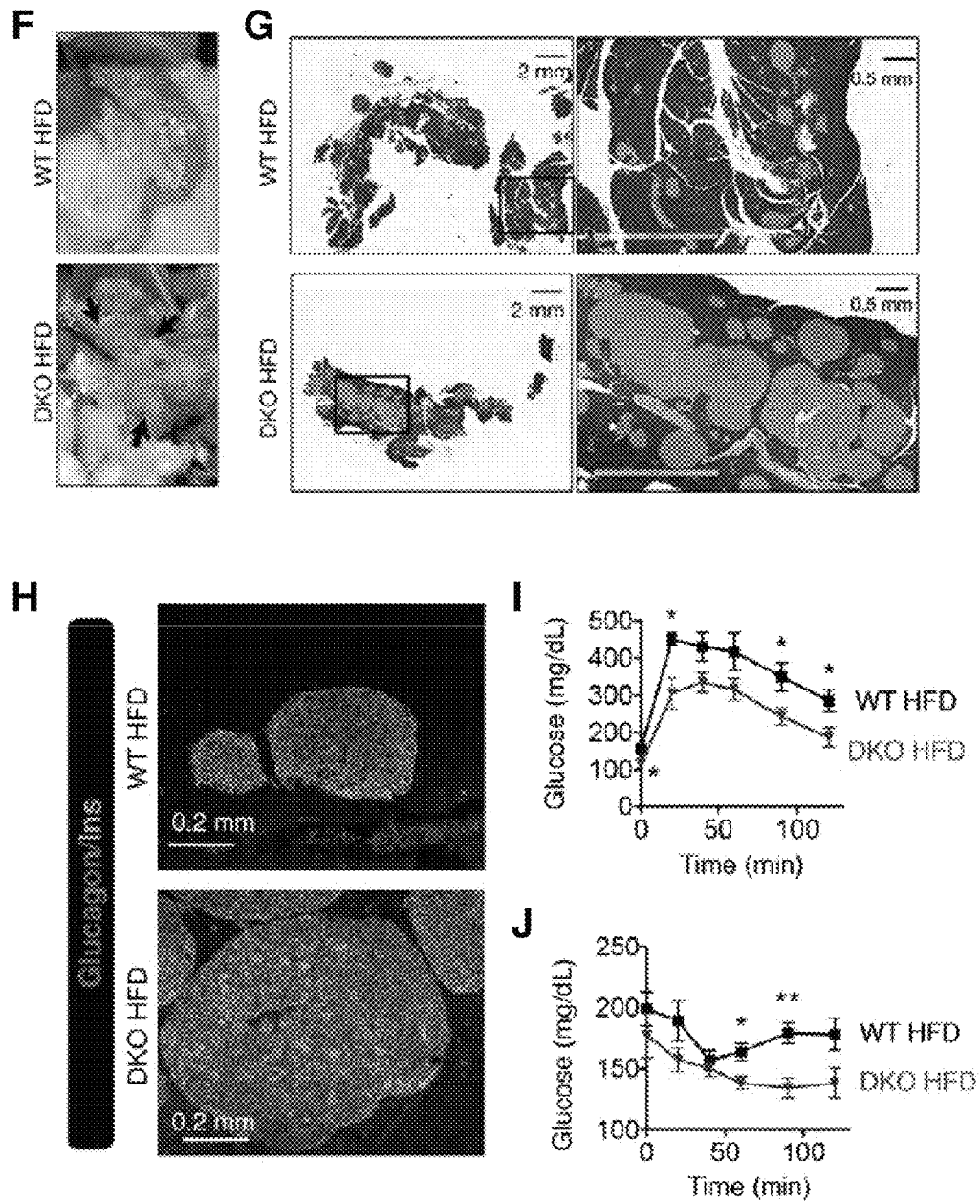

Mice with combined Tlr2 and Tlr4 deficiency (DKO) fed a HFD grew comparably to the WT cohorts fed a HFD, but following prolonged feeding of a HFD, DKO mice became slightly more obese with doubling of the epididymal fat pad weight. Multiplex ELISA for several key circulating metabolic hormones revealed that the insulin level was significantly increased in DKO mice compared to WT cohorts fed a HFD, whereas other hormones were slightly increased or unchanged, including glucagon, glucagon-like peptide (GLP-1), leptin, resistin, and ghrelin. Serum insulin levels indeed increased progressively in DKO mice following a HFD compared to WT mice on the same diet (FIG. 1C). Unlike WT mice, which developed hyperglycemia on the HFD, DKO mice remained normoglycemic (FIG. 1D). Strikingly, histological examination of the pancreas revealed that pancreata from DKO mice had progressively enlarged islets and β cell mass (FIG. 1E). After prolonged 51-week HFD feeding, islets from DKO mice were visible with the naked eye (FIG. 1F), fused together and became pervasive (FIG. 1G). These massive islets in DKO mice were due to a specific expansion of β cells (FIG. 1H), not a cells (FIG. 1H).

Example 4

Effects of Aging and HFD on Islet Expansion

To distinguish aging vs. HFD effects on islet expansion, islet mass from young and old WT and DKO mice on LFD was analyzed. Islet sizes and β cell mass were comparable between the two cohorts on LFD for up to 45 weeks, suggesting that the effect of TLR2/TLR4 deficiency on β cell mass expansion is HFD dependent. Further, islet hyperplasia and hyperinsulinemia in DKO mice were not caused by glucose intolerance and insulin resistance as reported in the liver-specific insulin receptor knockout (LIRKO) mice (Kahn, C. R. et al., *Diabetes*, 43, 1066-1084 (1994)). Indeed, DKO mice fed on a HFD had improved glucose tolerance and insulin sensitivity (FIGS. 1I-1J), with ameliorated hepatic steatosis, consistent with an elevated functional β cell capacity.

Example 5

Bone Marrow Transplantation (BMT) Experiments

β cell mass expansion can be controlled in a non-cell autonomous manner by immune cells in a paracrine fashion (Dirice, E. et al., *Diabetes*, 63, 188-202 (2014); Xiao, X. et al., *Proc Natl Acad Sci USA*, 111, E1211-1220 (2014); Jourdan, T. et al., *Nat Med*, 19, 1132-1140 (2013)) or by hepatokines in an endocrine fashion (El Ouaamari, A. et al., *Cell Reports*, 3, 401-410 (2013); Escribano, O. et al., *Diabetes*, 58, 820-828 (2009)).

Figures 2A, 2B:
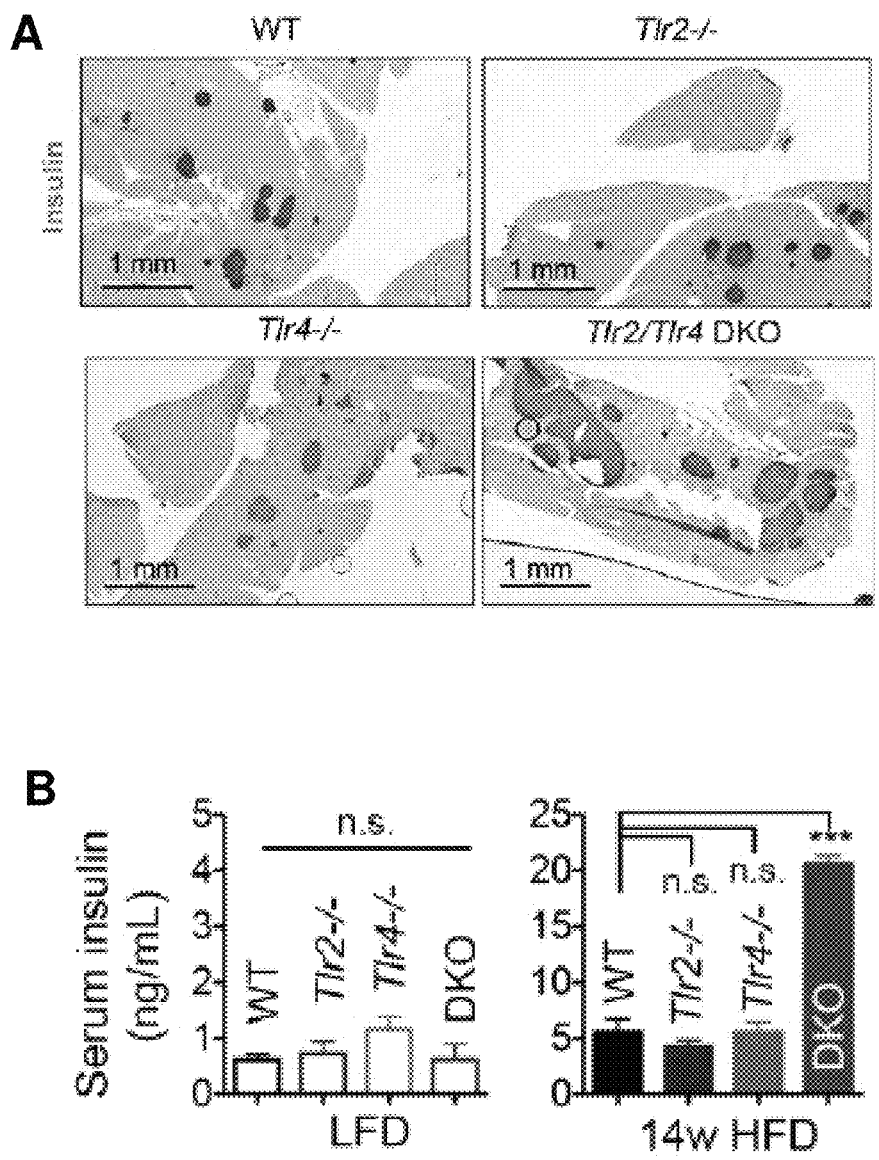
FIGS. 2A-2J. The effect of TLR2 and TLR4 on islet mass expansion in obese mice is islet intrinsic. (A-B) Characterization of Tlr2 and Tlr4 single knockout mice: (A) Representative images of insulin in pancreatic tissue sections from mice fed with HFD for 14 weeks; (B) Serum insulin levels from mice fed with LFD or 14-week HFD. (C-E) Bone marrow transplantation (BMT) experiment: (C) Representative images of insulin in pancreatic sections. The quantification of insulin-positive areas normalized to the total pancreas area is shown in (D). (E) Serum insulin level after a 5-hour fast. (F-I) Islet transplantation under kidney capsules: (F) Representative light microscopic images of primary islets with comparable size from young DKO and WT mice fed a LFD used for transplantation. (G) Blood glucose of WT T1D recipients post-transplantation. (H-I) Representative images of islet grafts under the kidney capsules of WT (H) and DKO (I) recipients. (J) Representative H&E images of transplanted islet grafts (arrow) in WT recipients. The dotted line marks the boundary of the islets. (A-E), n=4-6 mice each; f-i, representative image from 4 mice each. Values represent mean±SEM. N.S, not significant; *, p<0.05; , p<0.01; *, p<0.001 by one-way ANOVA with Newman-Keuls post-test or two-tailed Student's t test (g).
Figures 2C, 2D, 2E:
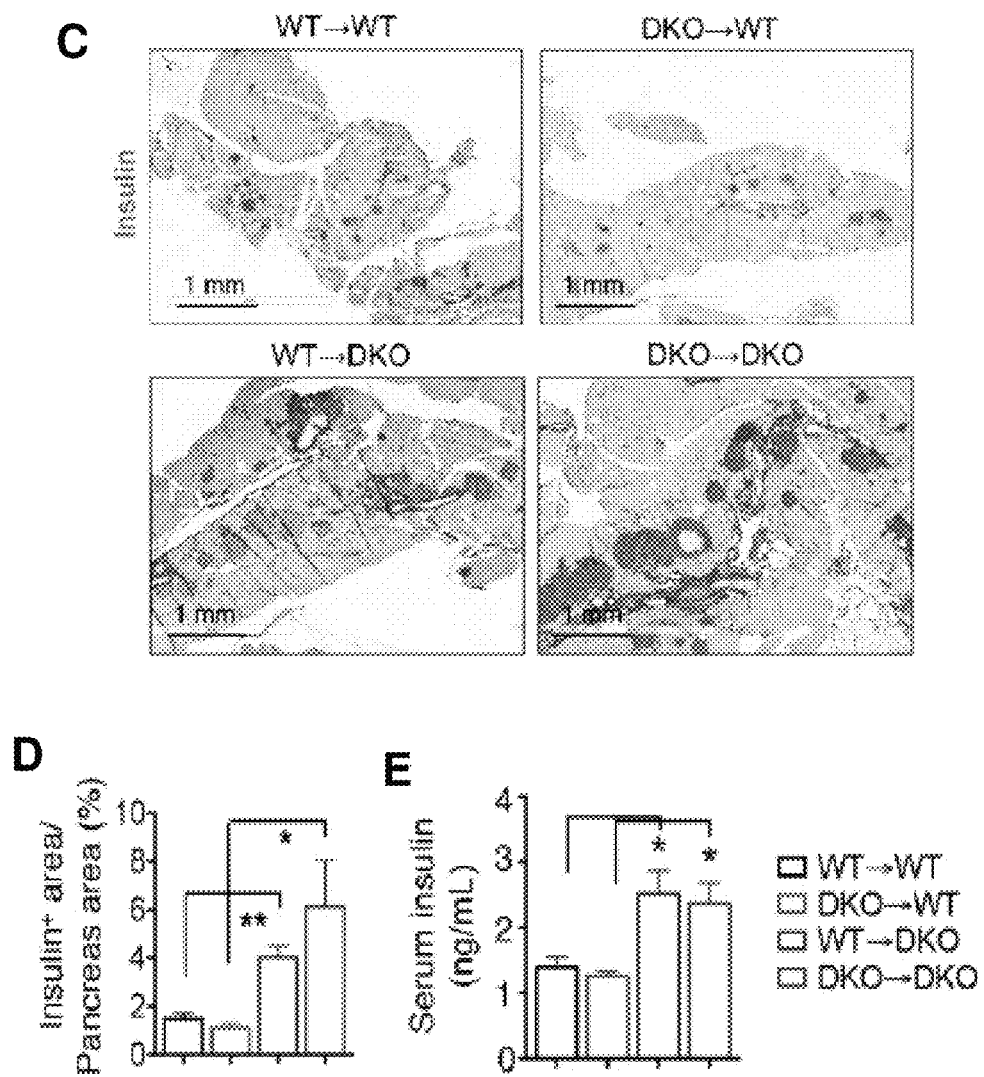
Figures 5A, 5B, 5C:
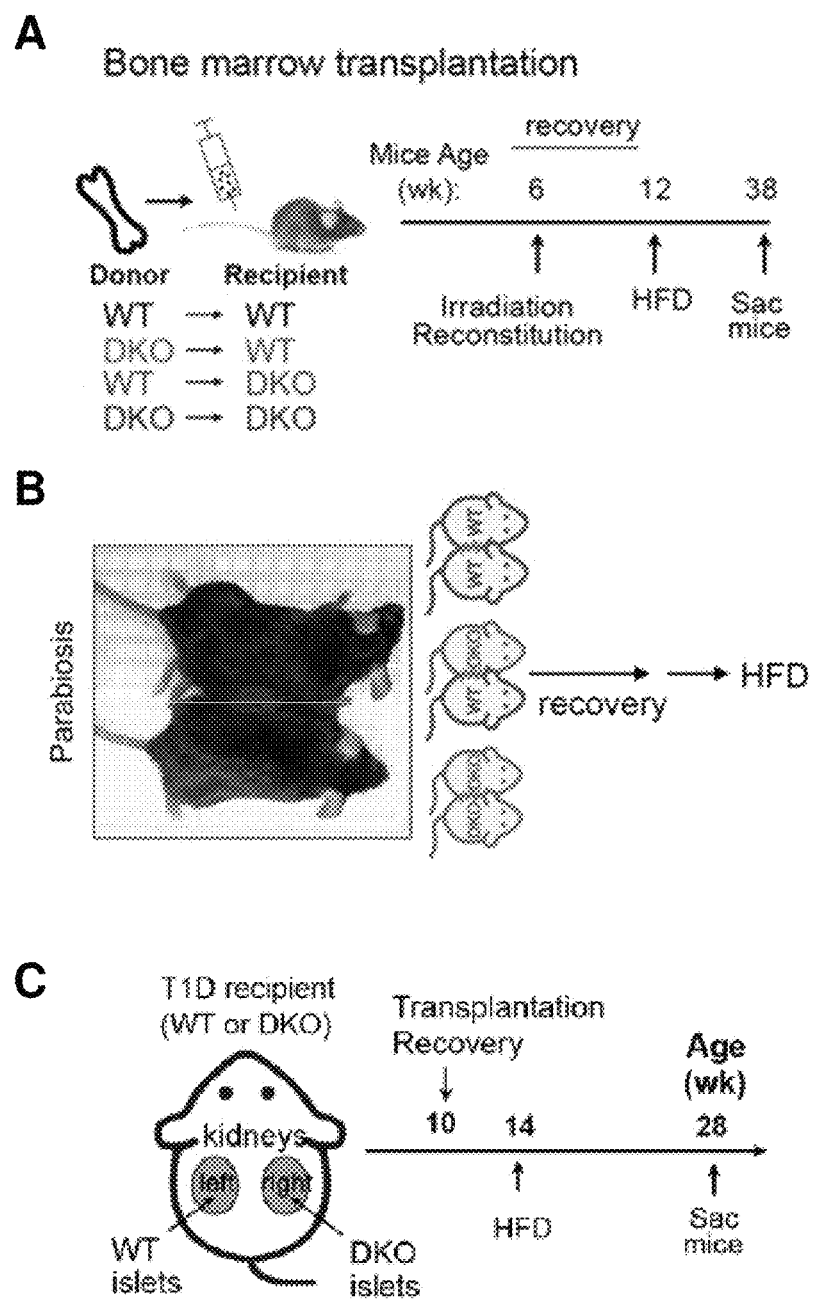
FIGS. 5A-5C. Experimental setups. (A) Schematic diagram for Bone marrow transplantation (BMT) experiment. (B) Experimental scheme for parabiosis and a picture of a surgically joined parabiotic pair. For parabiosis experiments, n=4-6 mice each, two repeats. (C) Schematic diagram of the islet transplantation in which 100 WT and 100 DKO primary islets were transplanted under the left and right kidney capsules, respectively, of streptozotocin (STZ)-induced diabetic recipients. The islets from WT and DKO mice were transplanted into the same recipient, either WT or DKO, to exclude potential contribution from the host. After a 4-week recovery, recipients were fed a HFD for 14 weeks prior to analysis.

Bone marrow transplantation (BMT) experiments were performed to discern whether hematopoietic TLR expression is responsible for β cell expansion. Four chimeric cohorts were generated using either WT mice (WT→WT and DKO→WT) or DKO mice (WT→DKO and DKO→DKO) as recipients (FIG. 5A). Chimeric mice were allowed to recover for 6 weeks prior to being fed a HFD for 26 weeks. Interestingly, regardless of the genotype of the donor, DKO recipients gained more weight on HFD but remained glucose tolerant. Furthermore, they exhibited increased islet and β cell masses and higher insulin levels than their WT counterparts (FIGS. 2C-2E). By contrast, glucagon-positive α cells and serum glucagon levels were comparable. Thus, hematopoietic immune cells are dispensable for diet-induced islet expansion in TLR2/TLR4 DKO mice.

This revelation was unexpected as much of the knowledge of TLR function has been centered on immune cells such as macrophages. Next, whether TLR2/TLR4 are expressed in islets or β cells was determined. Indeed, both Tlr2 and Tlr4 were expressed in islets as determined by real-time PCR. While Tlr4 expression level decreased in islets with age, Tlr2 level remained unchanged. More strikingly, TLR2 was significantly increased in the islets from T2D patients as compared to the healthy individuals. Furthermore, analysis of previous transcriptional profiling studies of various pancreatic cell types (Benitez, C. M. et al., *PLoS Genet*, 10, e1004645 (2014).) revealed increased expression of Tlr2 and Tlr4 in β cells during development. In 8-12-week-old adult mice, Tlr2 and Tlr4 expression in β cells were much higher than that in α cells. These data suggested a possible β cell-intrinsic role of TLR2/TLR4 in diet-induced β cell mass expansion.

Example 6

Parabiosis and Islet Transplantation Experiments

Parabiosis experiments were performed to assess the effect of a possible soluble factor(s) secreted by other tissues such as the liver (El Ouaamari, A. et al., *Cell Reports*, 3, 401-410 (2013); Escribano, O. et al., *Diabetes*, 58, 820-828 (2009)). WT and DKO mice were surgically joined to allow sharing of blood circulation and then placed on a HFD (FIG. 5B). The WT-DKO parabionts and two control pairs (DKO-DKO and WT-WT) exhibited similar body weight gain. Successful blood chimerism was confirmed using flow cytometry. The insulin-positive β cell mass in the WT parabiont was not affected by its DKO partner, and vice versa. Hence, these data excluded a major effect of a host-derived soluble factor(s) in islet expansion of HFD-fed DKO mice.

Figures 2F, 2G, 2H, 2I, 2J:
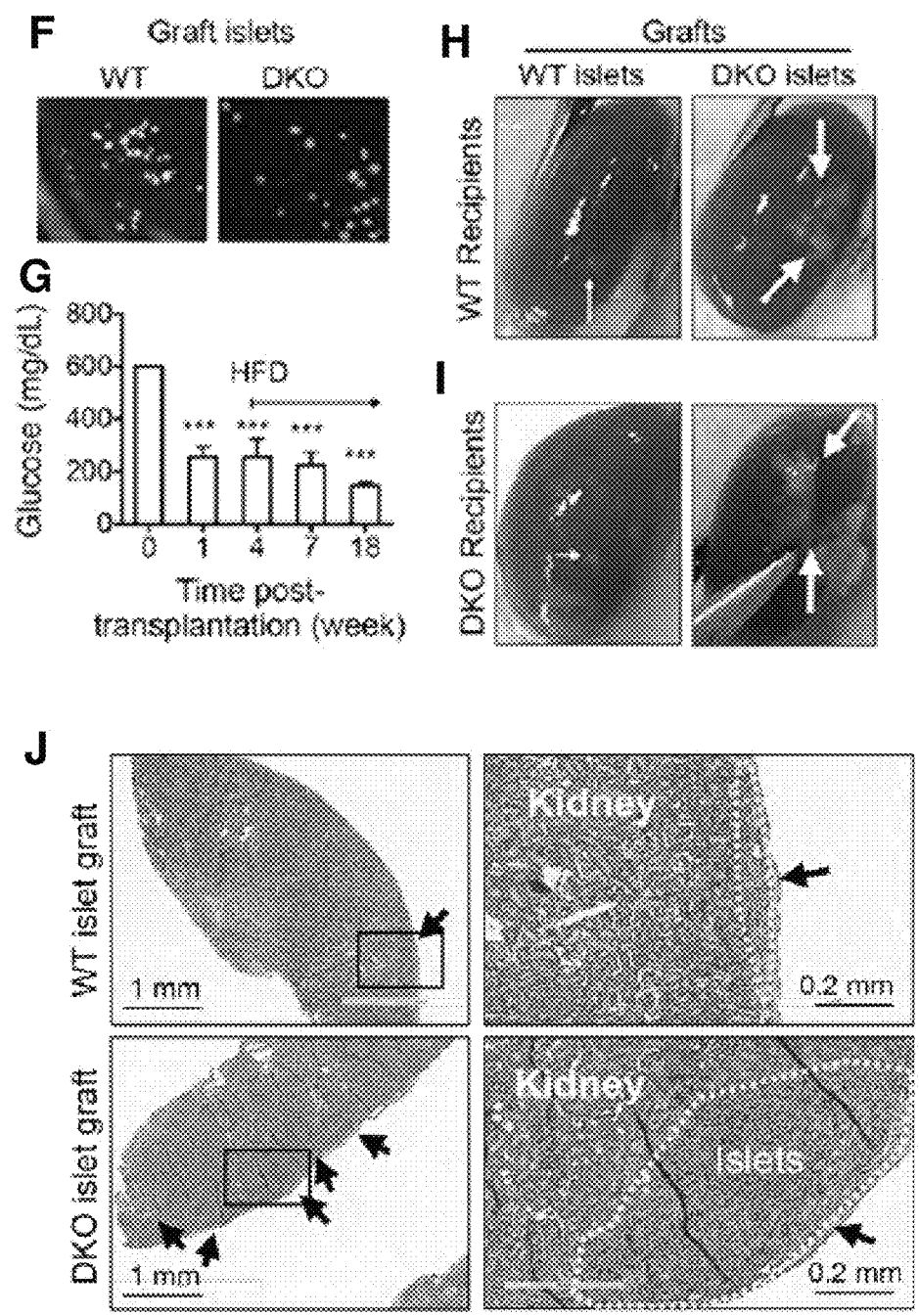

Next, islet transplantation was performed under kidney capsules to directly demonstrate a cell-autonomous effect of TLR2/TLR4 on islet expansion. Primary islets were transplanted from WT and DKO mice on a LFD with similar sizes (FIG. 2F) under the capsules of the left and right kidneys, respectively, of the same T1D recipients (WT or DKO mice treated with streptozotocin) (FIG. 5C). After islet transplantation and 4-week recovery, recipients were fed a HFD and gained weight; within days, blood glucose of the T1D recipients decreased (FIG. 2G), indicating successful transplantation. Strikingly, DKO islet grafts grew much larger than WT islet grafts in either WT or DKO recipients after 14 weeks on a HFD (FIGS. 2H-2I). Histological analyses revealed significantly larger islets and more insulin-positive cells in the DKO islet grafts compared to the WT islet grafts (FIG. 2J). Blood vascularization of the islet grafts under the kidney capsule was comparable between WT and DKO islets, excluding a possible contribution of vascularization in islet expansion (Brissova, M. et al., *Cell Metab*, 19, 498-511 (2014)). These data demonstrated that TLR2/TLR4 affect diet-induced islet expansion in an islet- or β cell-intrinsic manner.

Example 7

Etiology of Islet Expansion

Figure 3A:
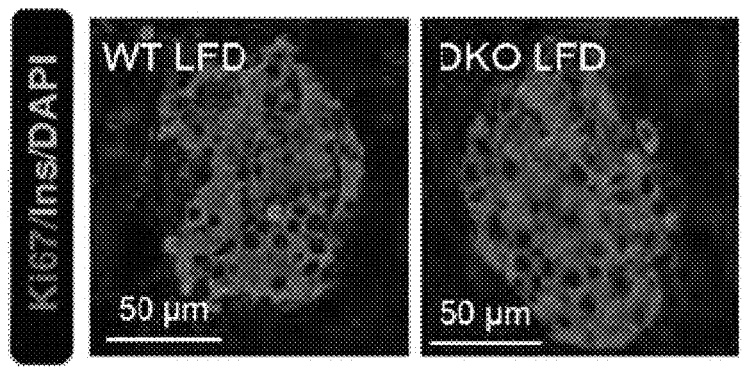
FIGS. 3A-3L. TLR2 and TLR4 deficiency triggers β cell proliferation and nuclear entry of Ccnd2 in a HFD-dependent manner. (A-C) Representative fluorescent images of Ki67 and insulin in mice fed a LFD (A) or HFD (B) for 14 weeks. (C) Percent of Ki67-positive β cells in mice on either LFD or HFD at different ages. Values represent mean±SEM. N.S, not significant; ***, p<0.001 by one-way ANOVA with Newman-Keuls post-test. (D) Representative fluorescent images of Ki67 and glucagon in pancreatic sections from mice after 14 weeks of HFD feeding. (E) Representative fluorescent images of Ki67 and insulin in DKO mice fed with HFD for 10 weeks followed by 4 weeks of LFD or HFD feeding. (F-G) Representative images showing Cyclin D2 localization in β (F) and α (G) cells of mice fed a HFD for 14-29 weeks. (H) Representative fluorescent images of Ccnd2 and insulin in DKO mice fed with HFD for 10 weeks followed by 4 weeks of LFD or HFD feeding. (I-J) Flow cytometric analysis of markers of β cell senescence, p16$^{INK4a}$ (I) and senescence-associated β-galactosidase (J), in mice after 39 weeks of HFD feeding. (K) Dynamic traces of insulin secretion of primary islets from WT and DKO mice following 9-week HFD in response to 14 mM glucose for 20 min and 30 mM KCl for 15 min. Representative experiment shown from 3 repeats with 50 islets/group. These experiments were performed after 9-week HFD to ensure that islets were about similar size between WT and DKO mice. (L) Representative transmission electron microscope (TEM) images of β cells from WT and DKO mice fed a HFD for 51 weeks. g, insulin granules; mito, mitochondria. a-d, N=3-6 mice each; c, ~200-400 β cells from 5-6 islets of LFD cohorts, and 2,000-7,300 β cells from 11-23 islets of HFD cohorts. E-J are representative data from 3-4 mice each with 2 repeats.
Figure 3B:
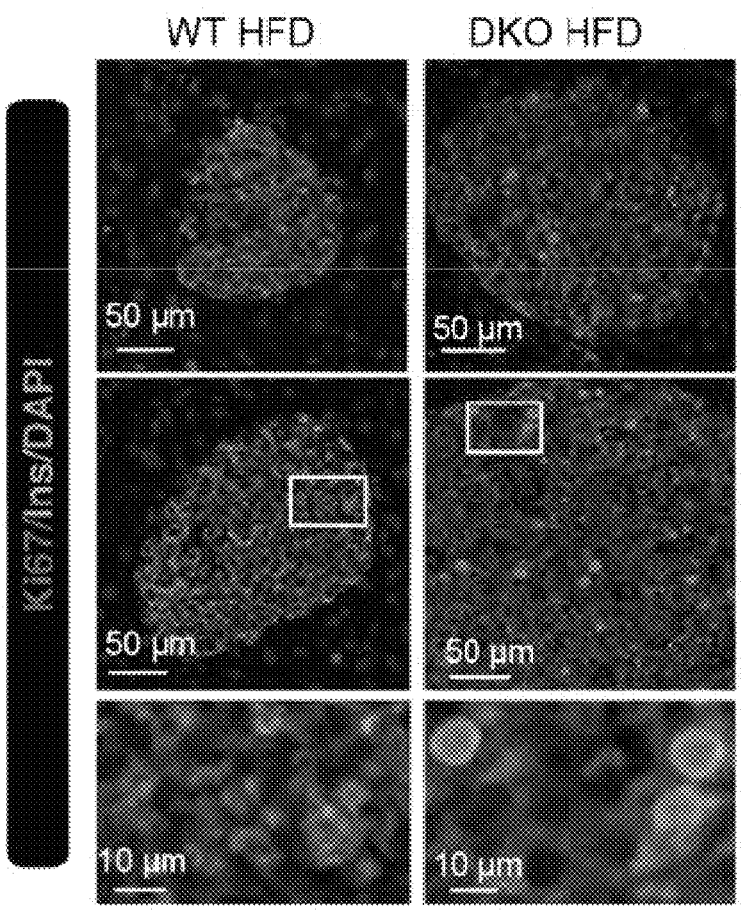
Figures 3C, 3D, 3E:
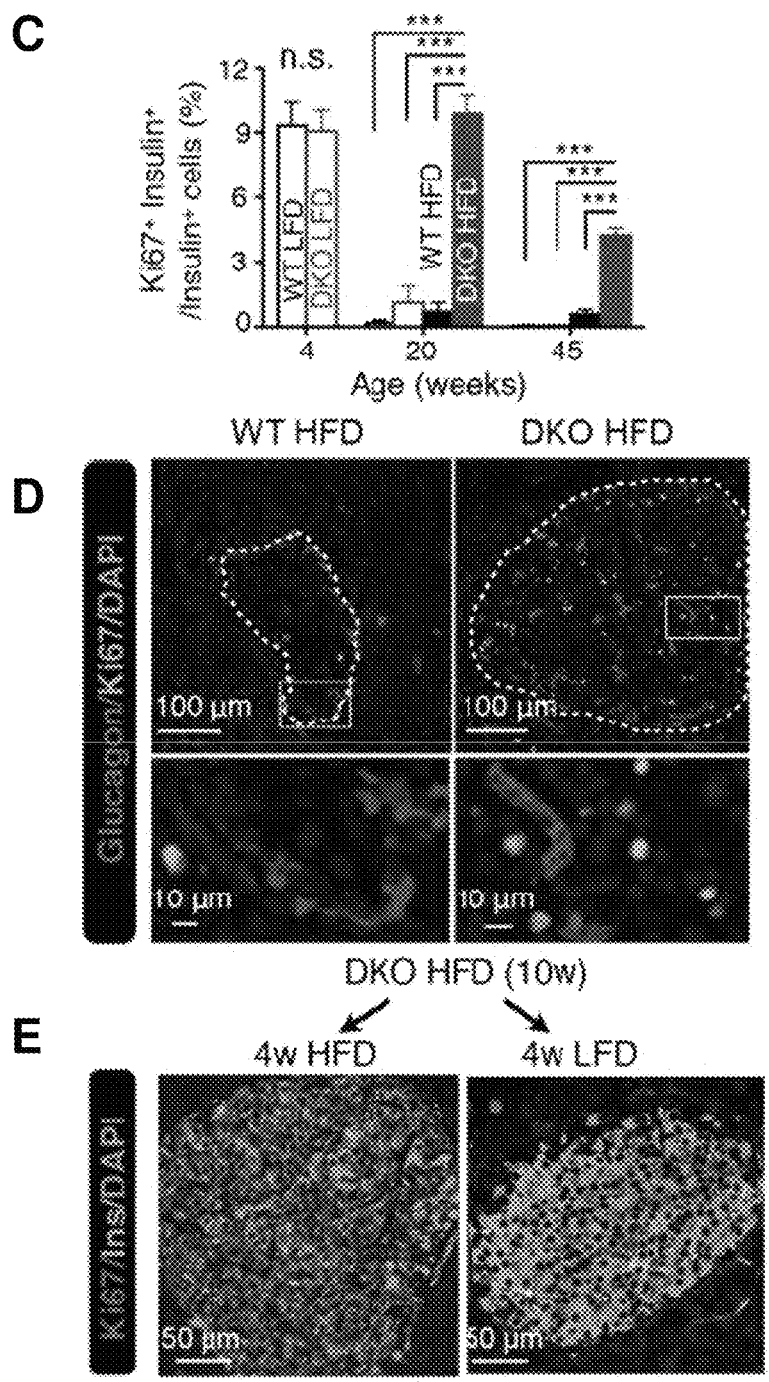

To assess the etiology of islet expansion, β cell proliferation was directly measured. After initial proliferative burst at 4 weeks of age which was similar between the WT and DKO cohorts, β cell proliferation in adult mice on LFD remained very low in both cohorts up to 45 weeks of age (FIG. 3A and quantitated in FIG. 3C). HFD feeding starting at 6 weeks of age moderately elevated β cell proliferation to approximately 0.6-0.7% in WT mice (FIG. 3B and quantitated in FIG. 3C); however, the proportion of proliferating DKO β cells was increased by 15- and 8-fold following 14 and 39 weeks on a HFD, respectively (FIG. 3B, and quantitated in FIG. 3C). Indeed, proliferation of DKO β cells following 14-week HFD was on par with that in neonates (FIG. 3C). Elevated β cell proliferation in HFD-fed DKO mice was further confirmed by the immunolabeling for proliferating cell nuclear antigen (PCNA) and pancreas/duodenum homeobox protein 1 (PDX1). Pointing to a β-cell specific effect, pancreatic α cells from DKO mice on a HFD were completely Ki67 negative (FIG. 3D), and so were the hepatocytes. Of note, there was no detectable β cell apoptosis in both groups as measured by TUNEL staining. Hence, it was concluded that disruption of TLR2/TLR4 signaling triggers β cell proliferation which accounts for profound islet mass expansion in DKO mice on a HFD.

Interestingly, β cell replication in DKO mice on a HFD for either 10 or 32 weeks was reversible following dietary switch to LFD for 4 weeks, which reduced β cell proliferation by more than 10-fold (FIG. 3E). Thus, together with normoglycemia of DKO mice on a HFD (FIG. 1D and FIG. 1I), these findings excluded the possibility of oncogenic transformation and development of insulinomas in DKO mice and demonstrated that with HFD, TLR2/TLR4 expression becomes a significant regulator of β cell replication and islet mass expansion.

Example 8

Figures 3F, 3G:
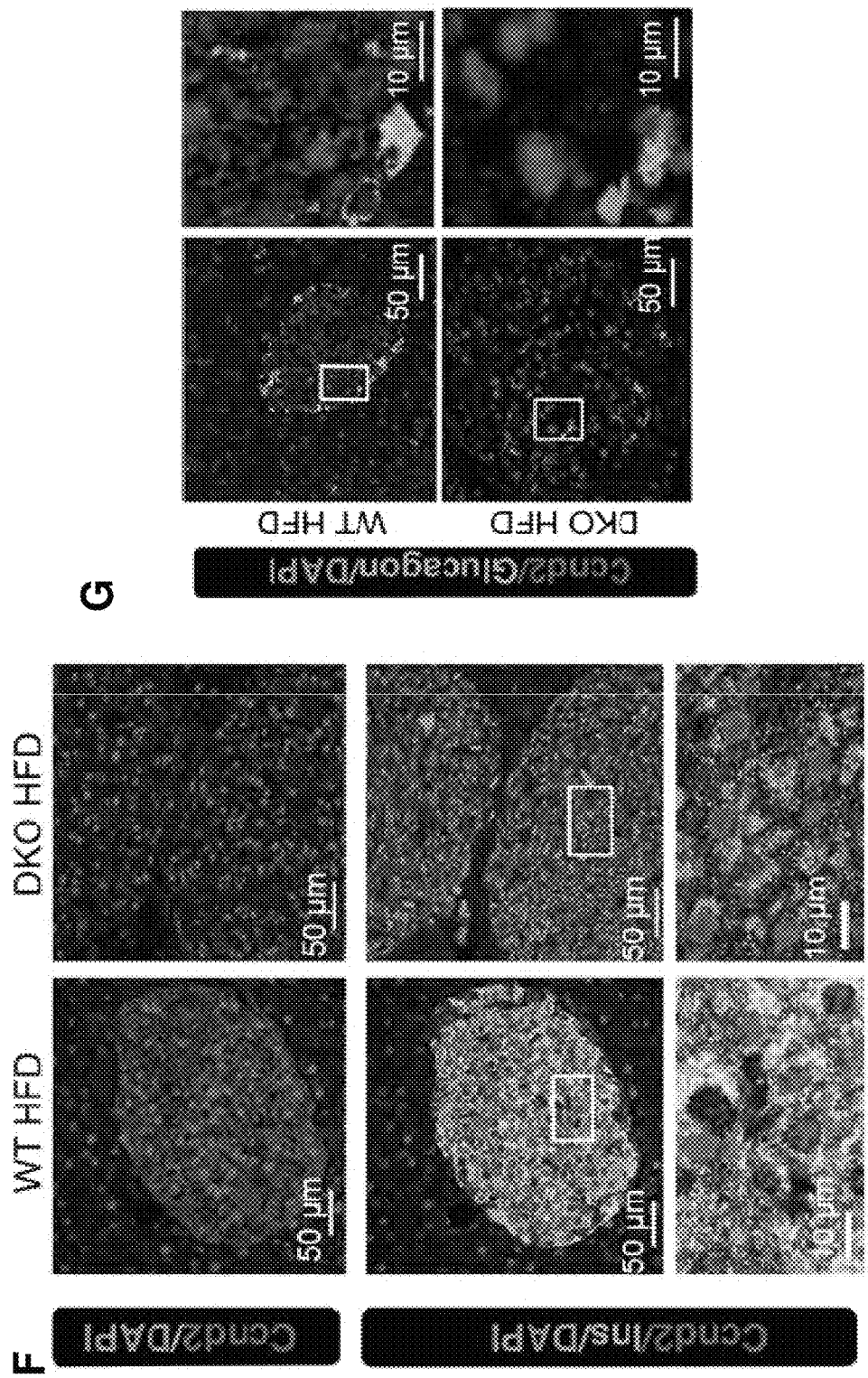
Figures 3H, 3I, 3J:
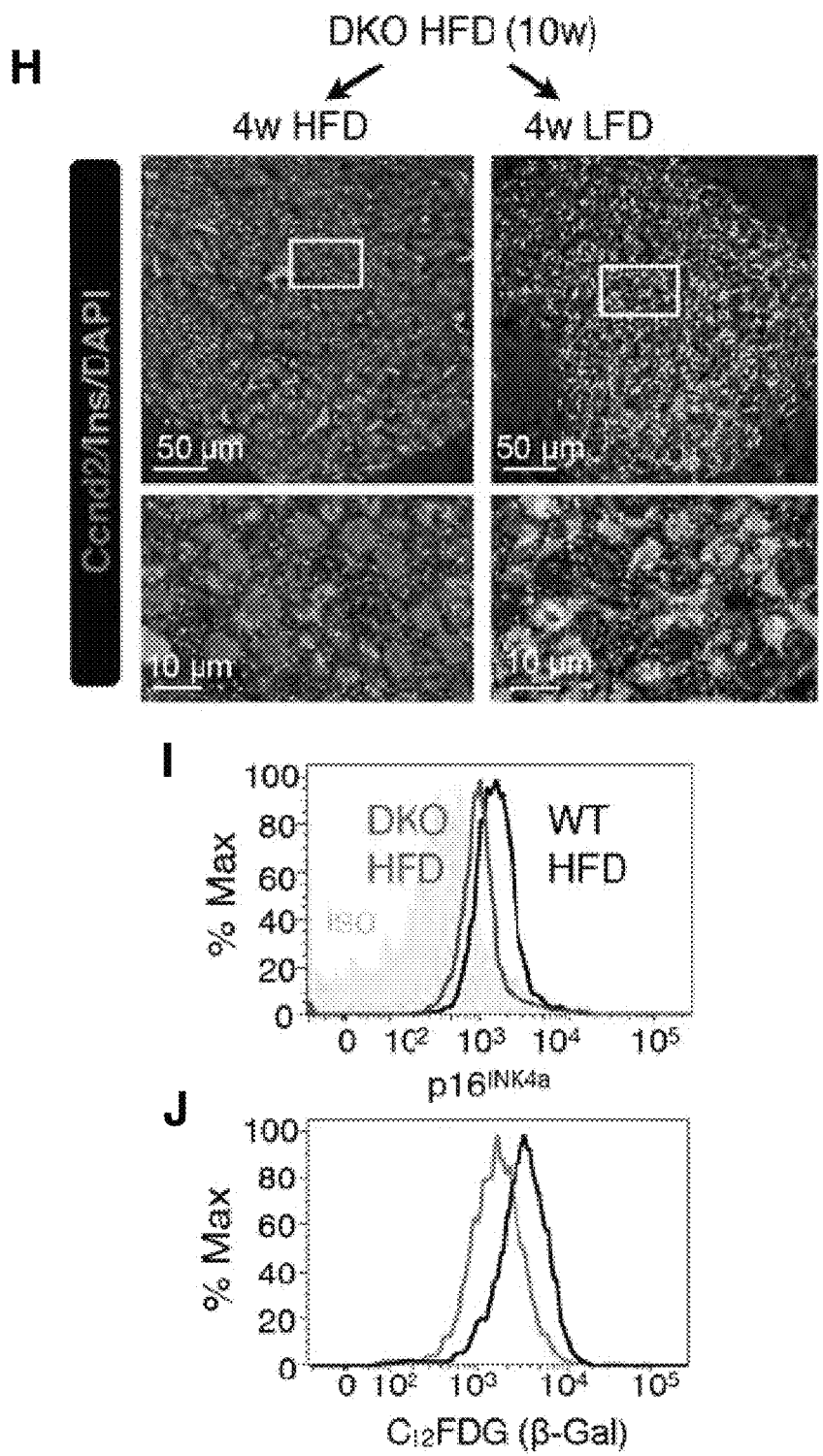
Figure 3K:
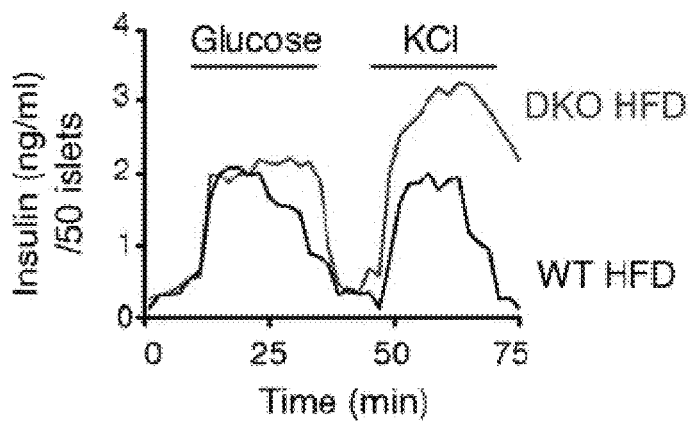
Figure 3L:
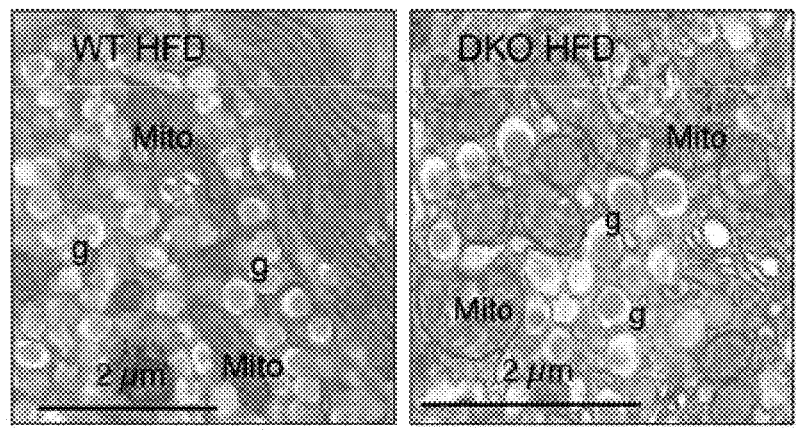

Molecular Events Leading to or Associated with Enhanced β Cell Proliferation in HFD-Fed DKO Mice Cyclin D2 protein, a well-known key regulator of compensatory β cell replication (Georgia, S. et al., *Diabetes*, 59, 987-996 (2010); Kushner, J. A. et al. *Mol Cell Biol*, 25, 3752-3762 (2005)), enters the nucleus to drive β cell cycle progression in both mice and humans (Fiaschi-Taesch, N. M. et al., *Diabetes*, 62, 2460-2470 (2013); Fiaschi-Taesch, N. M. et al., *Diabetes*, 62, 2450-2459 (2013)). Strikingly, Cyclin D2 was largely nuclear in β cells of HFD-fed DKO mice vs. largely cytosolic in WT islets (FIG. 3F). Providing further support to a β-cell specific effect, Cyclin D2 was not detectable in α cells (FIG. 3G). In keeping with the importance of HFD, nuclear accumulation of Cyclin D2 in DKO mice was significantly reduced upon switched to LFD for 4 weeks (FIG. 3H), and Cyclin D2 was largely cytosolic in DKO mice fed a LFD. Furthermore, elevated β cell proliferation in DKO mice was associated with decreased senescence compared to WT β cells following a 9-month HFD, as demonstrated by reduced expression of markers of cellular senescence, p16$^{INK4a}$ (Rane, S. G. et al., *Nat Genet*, 22, 44-52 (1999)) and senescence-associated β-galactosidase (FIGS. 3I-3J). In aggregate, we concluded that disruption of TLR2/TLR4 signaling triggers nuclear entry of Cyclin D2 in β cells, promotes β cell replication and reduces cellular senescence in diet-induced obesity.

β cell functionality for insulin production and regulated secretion was largely maintained in DKO mice on HFD when compared to that of WT mice, as measured by cytosolic calcium flux and insulin secretion (FIG. 3K) in response to extracellular stimuli such as glucose and KCl. Insulin granules in DKO β cells following 51-week HFD were largely normal and similar to those of WT β cells as assessed by transmission electron microscopy (FIG. 3L). Thus, replicating DKO β cells retain normal glucose regulatory function.

Example 9

Signaling Pathways Linking TLR2/TLR4 to Cyclin D2 and Proliferation in β Cells

Figures 6A, 6B, 6C, 6D, 6E:
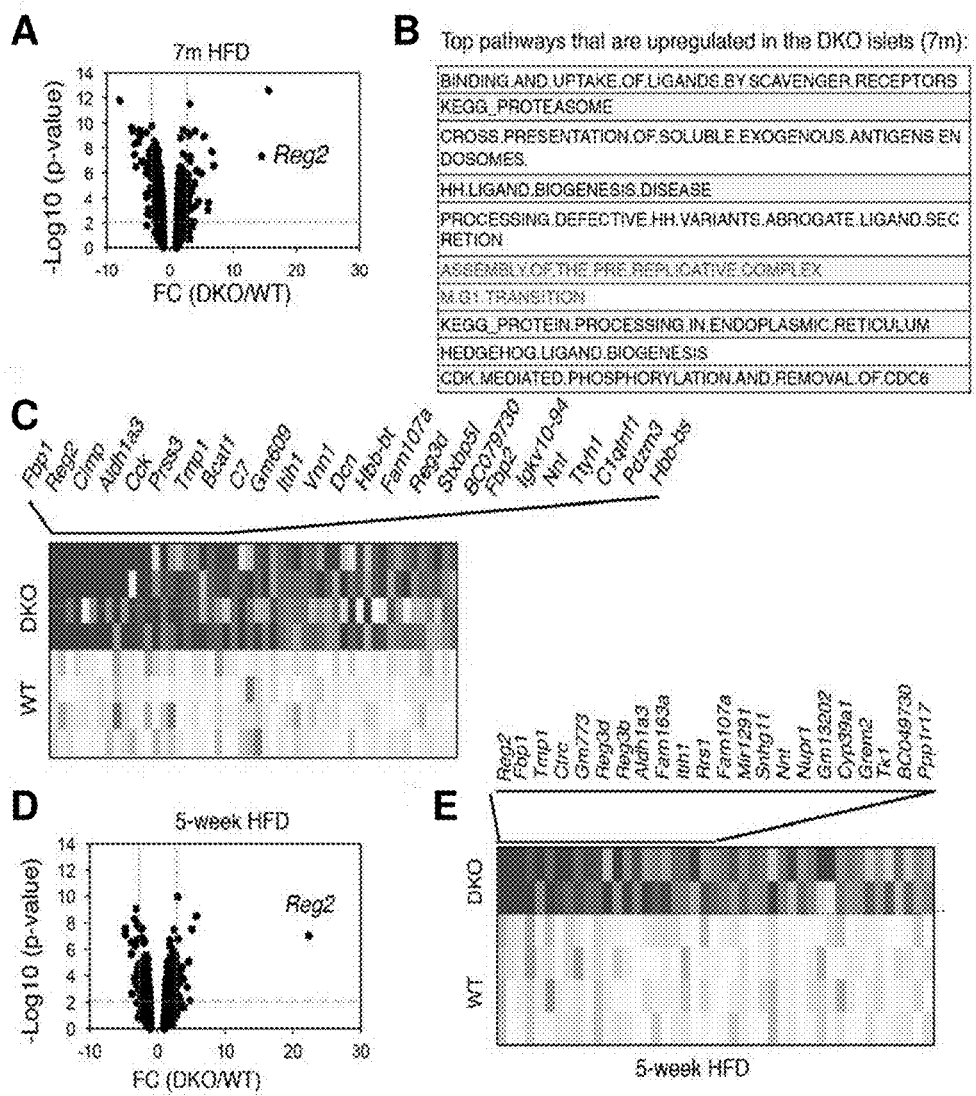
FIGS. 6A-6E. Microarray analysis of primary islets from WT and DKO mice on HFD reveals a unique signature of a highly proliferative β cell population. (A) Volcano plot comparing DKO and WT islets from mice on a HFD for 7 months (n=4 DKO and 4 WT mice). (B) GSEA analyses of the pathways affected by TLR2/TLR4 deficiency in islets of mice on HFD for 7 months. (C) Heat map showing upregulated genes (greater than 2.0 fold, p<0.01) in DKO compared to WT islets from mice on a HFD for 7 months. (D) A volcano plot comparing DKO and WT islets from mice on a HFD for 5 weeks (n=2 DKO and 4 WT mice). (E) Heatmap showing upregulated genes (over 2.0 fold, p<0.01) in DKO vs. WT islets from mice on 5-week HFD. Top genes are listed in both C and E.

At the outset, a non-biased global transcriptional profiling of islets from WT and DKO mice on a 7-month HFD was performed. Notably, loss of TLR2/TLR4 led to differential regulation of ~101 genes in islets whose levels were altered by more than 2.0 fold (False discovery rate, FDR q<0.05) (FIG. 6A). GSEA pathway analysis revealed a significant increase of pathways linked to cell cycle progression and replication in HFD-fed DKO islets (FIG. 6B), including the *Regenerating islet-derived gene* 2 (Reg 2), a gene highly induced in islet regeneration (Terazono, K. et al., *J Biol Chem*, 263, 2111-2114 (1988)) and required for compensatory islet proliferation and expansion in obesity and aging (Li, Q. et al., *Endocrinology*, en20161551 (2016)) (FIG. 6C). Similar results were obtained in islets following a short-term 5-week HFD (FIGS. 6D-6E). Therefore, these non-biased studies provided an equivocal evidence for a unique signature of a highly proliferative β cell population influenced by TLR2/TLR4 deletion in diet-induced obesity.

Figures 4A, 4B, 4C:
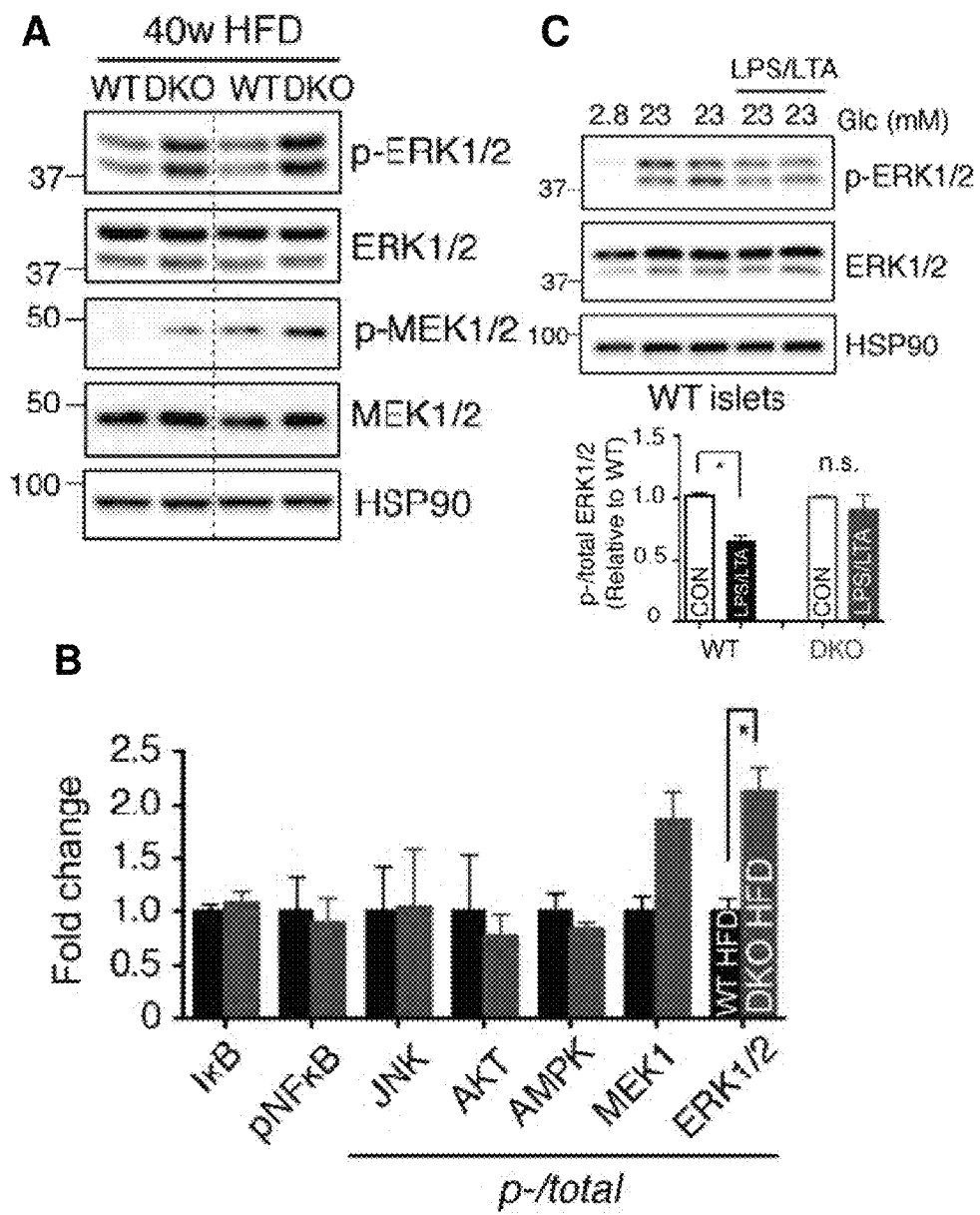
FIGS. 4A-4H. TLR2/TLR4 regulate β cell proliferation via the MEK/ERK pathway and the model. (A) Western blot analysis of the MEK/ERK pathway in islets from mice fed a HFD for 40 weeks, with quantitation shown in (B). Each lane, pooled islets from 3 mice. Dashed line marks separate experiments. (C) Western blot analysis of the MEK/ERK pathway in WT islets cultured in 2.8 or 22.8 mM glucose with or without LPS and LTA for 48 hr. Quantitation of p-ERK in total ERK shown below the blot. Each lane, pooled islets from 5 mice. (D-E) Representative fluorescent images of Ki67 (D) and Ccnd2 (E) in DKO mice on a HFD for 8 weeks treated with MEK162 for the last 2 days. Percentage of Ki67-positive β cells in 9-14 islets is shown below (D) with each symbol representing an islet. d-e, n=2 mice for CON and 4 mice for the MEK162 treatment group (two repeats). Values represent mean±SEM. ***, p<0.001 by two-tailed Student's t test. (F) Flow cytometric analysis of BrdU$^+$ β cells from Donor 1 human islets cultured in 2.8 mM (low) or 22.8 mM (high) glucose treated with or without LPS and LTA for 72 hr. BrdU was added in the last 48 hr. Percent of proliferating β cells is calculated as the ratio of BrdU$^+$ Insulin$^+$ cells (a) to total Insulin cells (a+b). (G) Quantitation of BrdU$^+$ β cells from three batches of human islets. A total of ~5,000 live cells were analyzed for each sample. (G) Model: In HFD-induced adaptive β cell expansion, TLR2/TLR4-mediated signaling pathways may counter the effect of β-cell tropic factors to limit β-cell proliferation. By disrupting TLR2/TLR4, a block on β cell proliferation is removed.
Figures 4D, 4E, 4F:
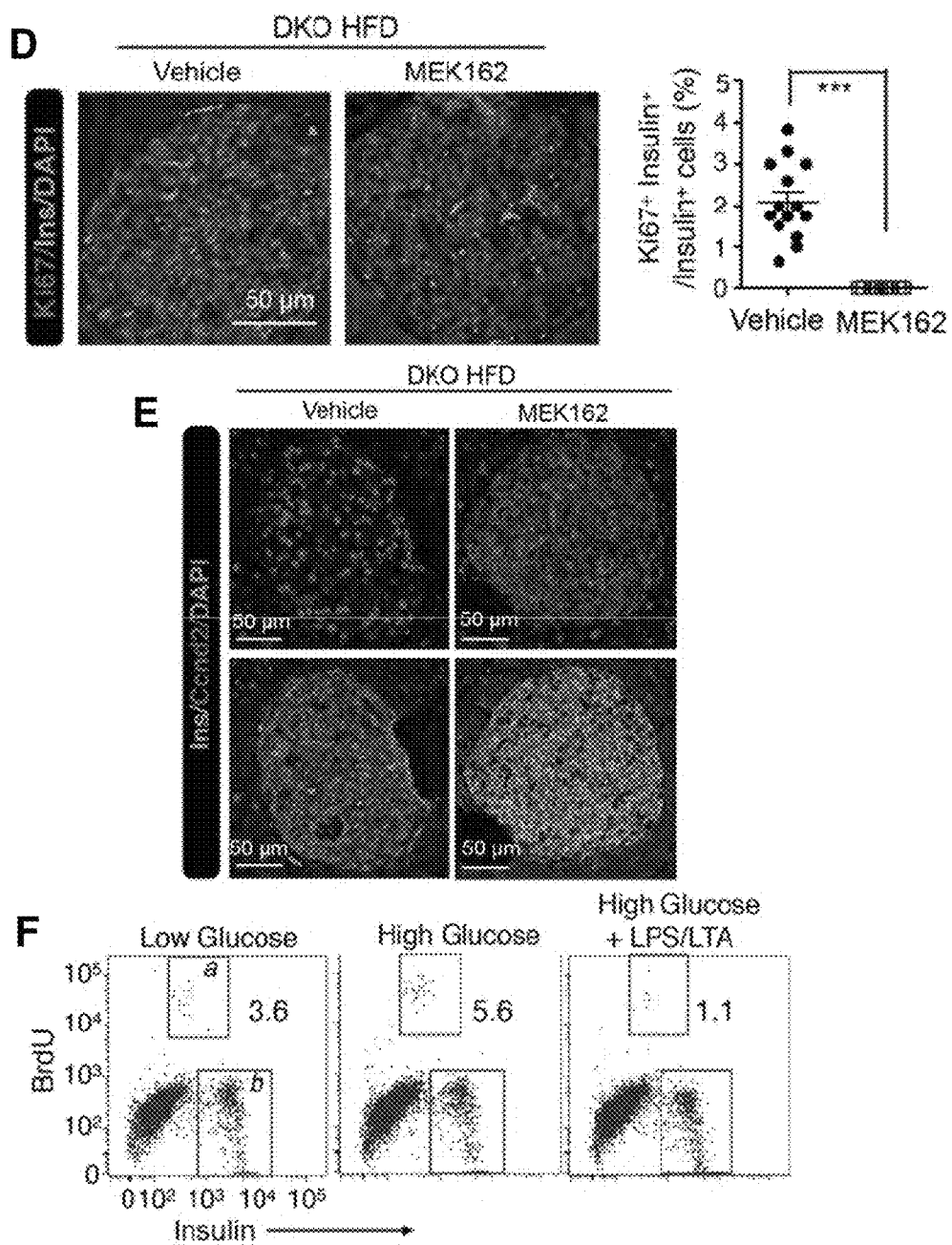
Figure 4G:
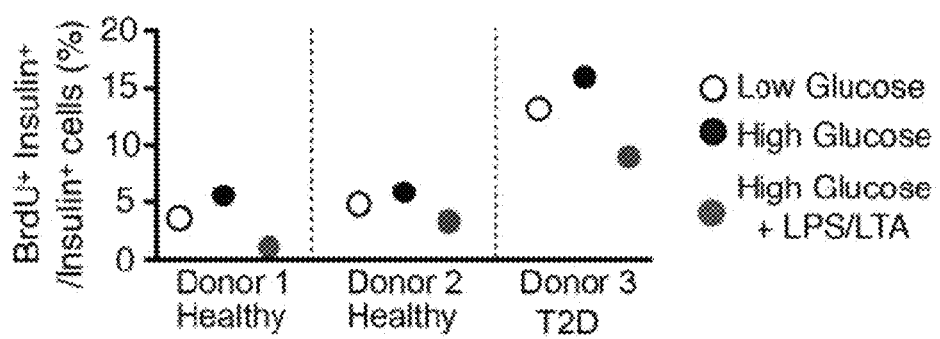

Next, the status of various signaling pathways that have been implicated in β cell proliferation was directly analyzed. Remarkably, phosphorylation of ERK1/2 proteins was increased by 2-3 fold in DKO islets from mice on HFD (FIG. 4A), while phosphorylation of other kinases including c-Jun amino-terminal kinases (JNK), AKT and AMP-activated protein kinase (AMPK) was unchanged. The upstream mitogen-activated protein kinase (MAPK) kinase 1/2 (MEK1/2) proteins were also hyperphosphorylated and activated in islets from DKO mice on a HFD (FIG. 4A). Quantitation is shown in FIG. 4B. These findings were further supported by the downregulation of p16$^{INK4a}$ protein level in DKO islets (FIG. 3I), a known downstream target of the ERK pathway in β cells (Chen, H. et al., *Nature*, 478, 349-355 (2011)). Conversely, LPS/LTA treatment suppressed ERK1/2 phosphorylation in WT islets in a TLR2/TLR4-dependent manner (FIG. 4C). Of note, LPS/LTA treatment in macrophages had the opposite effect on ERK phosphorylation, pointing to a cell type-specific effect of TLR2/TLR4 signaling on ERK signaling cascade. Further, LPS/LTA treatment reduced β cell proliferation in WT islets, but not DKO islets (FIG. 1B). Moreover, in vivo treatment with an oral small-molecule MEK inhibitor MEK162, a FDA approved drug known as Binimetinib, blocked ERK activation, abolished β cell proliferation and nuclear entry of Cyclin D2 in DKO mice fed a HFD (FIGS. 4D-4E). Lastly, in three different batches of human islets, activation of TLR2/TLR4 by LPS/LTA treatment consistently reduced hyperglycemia-induced β cell proliferation in both healthy and T2D individuals, albeit large variability among the samples in baseline proliferation (FIG. 4F and quantitated in FIG. 4G). Together, these in vitro and in vivo studies demonstrated that TLR2/TLR4 activation blocks the MEK/ERK signaling pathway and thereby attenuates proliferation in a β cell-intrinsic manner in both mice and humans.

Figure 4H:
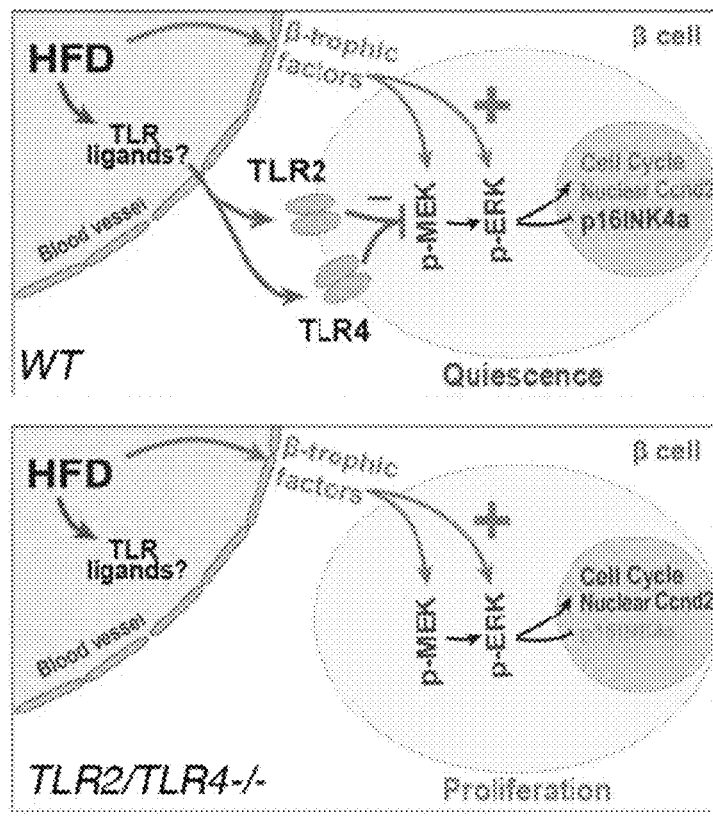

The data disclosed herein have uncovered a previous unknown regulatory mechanism underlying diet-induced β cell expansion. Based on these findings, it can be deduced that β cell proliferation is regulated by both positive and negative signals in diet-induced obesity, where positive signals provided by β-cell trophic factors such as nutrients, growth factors and/or insulin resistance are countered by negative signals exerted by HFD-mediated activation of TLR2/TLR4 (FIG. 4H). During chronic HFD feeding, TLR2/TLR4 can activate downstream pathways to down-regulate the MEK/ERK activation and reduce the nuclear entry of Ccnd2, thereby restraining adaptive β cell expansion. When TLR2/TLR4 are simultaneously disrupted (i.e. removing the brakes), β cell replication is propelled by the positive signal(s) and yet, maintain their characteristic features and functions (FIG. 4H). Although the data strongly point to a β cell-intrinsic TLR2/TLR4 signaling mechanism, the role of intra-islet paracrine signaling cannot be excluded. Moreover, although at best ~10% of β cells were proliferating in TLR2/TLR4 DKO mice on a HFD, it may be due to a snap shot of proliferating cells at the time of analysis and there are likely many more β cells that have entered the cell cycle during HFD.

TLR2 and TLR4 in immune cells have gained immense importance due to their ability to sense molecular patterns from invading pathogens and to bridge the innate and adaptive immune responses. The results of this disclosure expand this view by showing that TLR2/TLR4-mediated signaling pathways function together as a physiological regulator of adaptive β cell expansion during diet-induced obesity. These data suggest that TLR2 and TLR4 may integrate inflammatory signals in HFD-induced obesity to attenuate adaptive changes that governs β cell replication and permits facultative growth, hence revealing a previously underappreciated interplay between the metabolic and innate immune systems (Sun, S. et al., *Annu Rev Nutr*, 32, 261-286 (2012); Donath, M. Y et al., *Cell Metab*, 17, 860-872 (2013)). Purported activation of TLR2 and/or TLR4 by gut microbiota derivatives (Cani, P. D. et al., *Diabetes*, 56, 1761-1772 (2007); Cani, P. D. et al, *Diabetes*, 57, 1470-1481 (2008)) and/or fatty acids (Shi, H. et al., *J Clin Invest*, 116, 3015-3025 (2006)) may serve as a mechanism for limited β-cell mass expansion. Hence, β cell proliferation and circulating insulin levels may be more tightly linked to systemic inflammatory status than previously appreciated, thereby promoting cooperative and adaptive responses against diverse environmental challenges such as overnutrition.

What is claimed is:

1. A method for the treatment of diabetes in a subject, comprising providing insulin-producing cells to the subject, wherein the TLR2 and TLR4 genes in said cells have been inactivated.

2. The method of claim 1, wherein said providing comprises obtaining insulin-producing cells, inactivating the TLR2 and TLR4 genes in the obtained cells ex vivo, and transplanting the cells into the subject.

3. The method of claim 1, wherein said providing comprises inactivating the TLR2 and TLR4 genes in insulin-producing cells in the subject in vivo.

4. The method of claim 1, wherein the insulin-producing cells are cells of a pancreatic tissue.

5. The method of claim 4, wherein the insulin-producing cells are provided to the subject in the form of a pancreas, pancreatic islets or pancreatic β cells.

6. The method of claim 1, wherein the insulin-producing cells are derived from stem cells.

7. The method of claim 6, wherein said stem cells are selected from the group consisting of pancreatic stem cells, adult stem cells, induced pluripotent stem cells, embryonic stem cells, umbilical cord blood cells, amnion cells, placenta cells, umbilical cord vein cells, umbilical cord matrix cells, and progenitor-like stem cells.

8. The method of claim 6, wherein said insulin-producing cells are further induced to express PDX-1.

9. The method of claim 1, wherein the insulin-producing cells are derived from non-pancreatic cells.

10. The method of claim 9, wherein the insulin-producing cells are further induced to express PDX-1.

11. The method of claim 10, wherein the non-pancreatic cells are liver cells.

12. The method of claim 1, wherein the inactivation of the TLR2 and TLR4 genes in the cells is achieved by deleting or mutating the TLR2 and TLR4 genes in whole or in part such that no functional TLR2 or TLR4 protein product is expressed.

13. The method of claim 12, wherein the inactivation of the TLR2 and TLR4 genes in the cells is achieved by a method selected from the group consisting of CRISPR/Cas system, Cre/Lox system, TALEN system and homologous recombination.

14. The method of claim 1, wherein the inactivation of the TLR2 and TLR4 genes in the cells is achieved by blocking the signaling of TLR2 and TLR4 using an oxidized phospholipid.

15. The method of claim 14, wherein the phospholipid has the chemical structure:

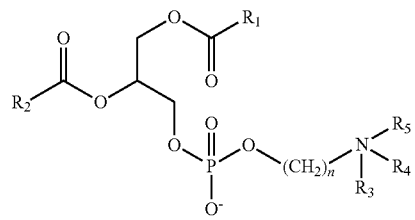

wherein:

$R_1$ is $C_{10}$-$C_{22}$ alkyl;

$R_2$ is $C_{10}$-$C_{22}$ alkenyl having 1-6 double bonds;

$R_3$, $R_4$ and $R_5$ are independently hydrogen or $C_1$-$C_{12}$ alkyl; and n is an integer from 1-4.

16. The method of claim 15, wherein the phospholipid has the chemical structure:

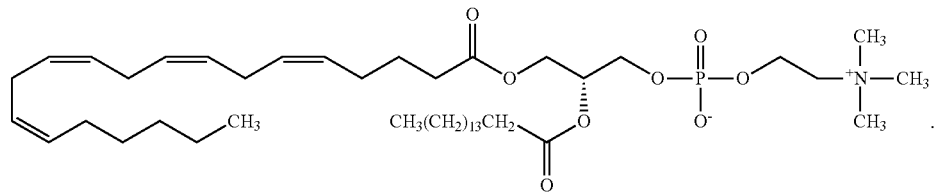

17. The method of claim 1, wherein the inactivation of the TLR2 and TLR4 genes in the cells is achieved by blocking the signaling of TLR2 and TLR4 using a combination of a TLR2 inhibitory compound and a TLR4 inhibitory compound.

18. The method of claim 17, wherein the TLR2 inhibitory compound has the chemical structure:

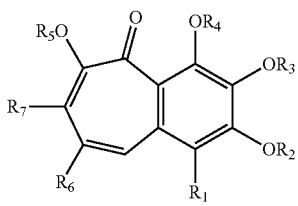

wherein:

$R_1$ and $R_7$ is hydrogen or $C_1$-$C_{12}$ alkyl;

$R_2$, $R_3$, $R_4$ and $R_5$ are independently hydrogen, $C_1$-$C_{12}$ alkyl, or $C_3$-$C_{12}$ cycloalkyl;

$R_6$ is $COOR_8$, $CONHR_8$; and $R_8$ is hydrogen, $C_1$-$C_{20}$ alkyl, or aryl.

19. The method of claim 18, wherein the compound has the chemical structure:

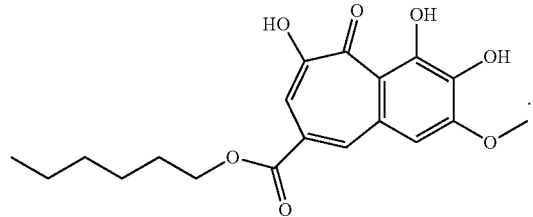 [SMILES: CCCCCCOC(=O)c1cc(O)c(=O)c2c(O)c(O)c(OC)cc2c1]

20. The method of claim 17, wherein the TLR4 inhibitory compound has the chemical structure:

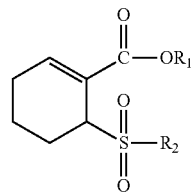

wherein:
$R_1$ is $C_1$-$C_{12}$ alkyl;
$R_2$ is $(CH_2)_n$—$R_3$, or N—$R_3R_4$;
$R_3$ is aryl or substituted aryl having at least one halogen substituent;
$R_4$ is hydrogen or $C_1$-$C_{12}$ alkyl, and
n is an integer from 1 to 4.

21. The method of claim 20, wherein the compound has the chemical structure:

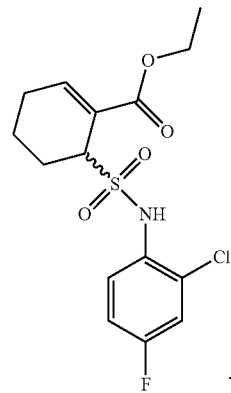 [SMILES: CCOC(=O)C1=CCCCC1S(=O)(=O)Nc1ccc(F)cc1Cl]

* * * * *

SEQUENCE LISTING

```
<160> NUMBER OF SEQ ID NOS: 40

<210> SEQ ID NO 1
<211> LENGTH: 22
<212> TYPE: DNA
<213> ORGANISM: Artificial Sequence
<220> FEATURE:
<223> OTHER INFORMATION: Oligonucleotide

<400> SEQUENCE: 1
tcagccgatt tgctatctca ta                                    22

<210> SEQ ID NO 2
<211> LENGTH: 22
<212> TYPE: DNA
<213> ORGANISM: Artificial Sequence
<220> FEATURE:
<223> OTHER INFORMATION: Oligonucleotide

<400> SEQUENCE: 2
agtacttggg cagattgacc tc                                    22

<210> SEQ ID NO 3
<211> LENGTH: 21
<212> TYPE: DNA
<213> ORGANISM: Artificial Sequence
<220> FEATURE:
<223> OTHER INFORMATION: Oligonucleotide

<400> SEQUENCE: 3
gagcaacaag aaaaccaagc a                                     21

<210> SEQ ID NO 4
<211> LENGTH: 21
<212> TYPE: DNA
<213> ORGANISM: Artificial Sequence
<220> FEATURE:
<223> OTHER INFORMATION: Oligonucleotide

<400> SEQUENCE: 4
tgcacacaag ccatctactc a                                     21

<210> SEQ ID NO 5
<211> LENGTH: 20
<212> TYPE: DNA
<213> ORGANISM: Artificial Sequence
<220> FEATURE:
<223> OTHER INFORMATION: Oligonucleotide

<400> SEQUENCE: 5
agatgcccac tgctgatagg                                       20

<210> SEQ ID NO 6
<211> LENGTH: 20
<212> TYPE: DNA
<213> ORGANISM: Artificial Sequence
<220> FEATURE:
<223> OTHER INFORMATION: Oligonucleotide

<400> SEQUENCE: 6
ttggcacgat tctcagcata                                       20

<210> SEQ ID NO 7
<211> LENGTH: 21
<212> TYPE: DNA
<213> ORGANISM: Artificial Sequence
```

```
<220> FEATURE:
<223> OTHER INFORMATION: Oligonucleotide

<400> SEQUENCE: 7
catcctgctc tcatgcctga t                                              21

<210> SEQ ID NO 8
<211> LENGTH: 21
<212> TYPE: DNA
<213> ORGANISM: Artificial Sequence
<220> FEATURE:
<223> OTHER INFORMATION: Oligonucleotide

<400> SEQUENCE: 8
gcagatggca ggtcttcttc a                                              21

<210> SEQ ID NO 9
<211> LENGTH: 20
<212> TYPE: DNA
<213> ORGANISM: Artificial Sequence
<220> FEATURE:
<223> OTHER INFORMATION: Oligonucleotide

<400> SEQUENCE: 9
ttttgccaga acatgaatgc                                                20

<210> SEQ ID NO 10
<211> LENGTH: 20
<212> TYPE: DNA
<213> ORGANISM: Artificial Sequence
<220> FEATURE:
<223> OTHER INFORMATION: Oligonucleotide

<400> SEQUENCE: 10
gtgccaacga cggttacttt                                                20

<210> SEQ ID NO 11
<211> LENGTH: 20
<212> TYPE: DNA
<213> ORGANISM: Artificial Sequence
<220> FEATURE:
<223> OTHER INFORMATION: Oligonucleotide

<400> SEQUENCE: 11
ggcttcattc ttgtcctcca                                                20

<210> SEQ ID NO 12
<211> LENGTH: 20
<212> TYPE: DNA
<213> ORGANISM: Artificial Sequence
<220> FEATURE:
<223> OTHER INFORMATION: Oligonucleotide

<400> SEQUENCE: 12
agatgggttc ctctcccagt                                                20

<210> SEQ ID NO 13
<211> LENGTH: 20
<212> TYPE: DNA
<213> ORGANISM: Artificial Sequence
<220> FEATURE:
<223> OTHER INFORMATION: Oligonucleotide

<400> SEQUENCE: 13
gtgttgcctg atgtcccttt                                                20
```

<210> SEQ ID NO 14
<211> LENGTH: 20
<212> TYPE: DNA
<213> ORGANISM: Artificial Sequence
<220> FEATURE:
<223> OTHER INFORMATION: Oligonucleotide

<400> SEQUENCE: 14
ttagcccagg tctgtggttc                                              20

<210> SEQ ID NO 15
<211> LENGTH: 23
<212> TYPE: DNA
<213> ORGANISM: Artificial Sequence
<220> FEATURE:
<223> OTHER INFORMATION: Oligonucleotide

<400> SEQUENCE: 15
ttctctgtac catgacactc tgc                                          23

<210> SEQ ID NO 16
<211> LENGTH: 21
<212> TYPE: DNA
<213> ORGANISM: Artificial Sequence
<220> FEATURE:
<223> OTHER INFORMATION: Oligonucleotide

<400> SEQUENCE: 16
cgtggaatct tccggctgta g                                            21

<210> SEQ ID NO 17
<211> LENGTH: 22
<212> TYPE: DNA
<213> ORGANISM: Artificial Sequence
<220> FEATURE:
<223> OTHER INFORMATION: Oligonucleotide

<400> SEQUENCE: 17
aatccggaat ctaagaccat ca                                           22

<210> SEQ ID NO 18
<211> LENGTH: 22
<212> TYPE: DNA
<213> ORGANISM: Artificial Sequence
<220> FEATURE:
<223> OTHER INFORMATION: Oligonucleotide

<400> SEQUENCE: 18
gcaattagga ctagccatcc ac                                           22

<210> SEQ ID NO 19
<211> LENGTH: 22
<212> TYPE: DNA
<213> ORGANISM: Artificial Sequence
<220> FEATURE:
<223> OTHER INFORMATION: Oligonucleotide

<400> SEQUENCE: 19
ggctcaagga caacaattta gg                                           22

<210> SEQ ID NO 20
<211> LENGTH: 22
<212> TYPE: DNA
<213> ORGANISM: Artificial Sequence
<220> FEATURE:
<223> OTHER INFORMATION: Oligonucleotide

```
<400> SEQUENCE: 20
actgtggaaa aaccgttgaa ct                                              22

<210> SEQ ID NO 21
<211> LENGTH: 20
<212> TYPE: DNA
<213> ORGANISM: Artificial Sequence
<220> FEATURE:
<223> OTHER INFORMATION: Oligonucleotide

<400> SEQUENCE: 21
tatgaacaga tgggcctcct                                                 20

<210> SEQ ID NO 22
<211> LENGTH: 20
<212> TYPE: DNA
<213> ORGANISM: Artificial Sequence
<220> FEATURE:
<223> OTHER INFORMATION: Oligonucleotide

<400> SEQUENCE: 22
agctgggttc tccacctctt                                                 20

<210> SEQ ID NO 23
<211> LENGTH: 23
<212> TYPE: DNA
<213> ORGANISM: Artificial Sequence
<220> FEATURE:
<223> OTHER INFORMATION: Oligonucleotide

<400> SEQUENCE: 23
ggagtatttc tacaccagca gca                                             23

<210> SEQ ID NO 24
<211> LENGTH: 22
<212> TYPE: DNA
<213> ORGANISM: Artificial Sequence
<220> FEATURE:
<223> OTHER INFORMATION: Oligonucleotide

<400> SEQUENCE: 24
acagggaagc tatacagggt ca                                              22

<210> SEQ ID NO 25
<211> LENGTH: 20
<212> TYPE: DNA
<213> ORGANISM: Artificial Sequence
<220> FEATURE:
<223> OTHER INFORMATION: Oligonucleotide

<400> SEQUENCE: 25
ttgtgccaag tctggagatg                                                 20

<210> SEQ ID NO 26
<211> LENGTH: 20
<212> TYPE: DNA
<213> ORGANISM: Artificial Sequence
<220> FEATURE:
<223> OTHER INFORMATION: Oligonucleotide

<400> SEQUENCE: 26
ttctcagagc ggatgaaggt                                                 20

<210> SEQ ID NO 27
```

```
<211> LENGTH: 20
<212> TYPE: DNA
<213> ORGANISM: Artificial Sequence
<220> FEATURE:
<223> OTHER INFORMATION: Oligonucleotide

<400> SEQUENCE: 27
tcattgaaag ccaaacatcg                                              20

<210> SEQ ID NO 28
<211> LENGTH: 20
<212> TYPE: DNA
<213> ORGANISM: Artificial Sequence
<220> FEATURE:
<223> OTHER INFORMATION: Oligonucleotide

<400> SEQUENCE: 28
cctggggagc tgtatttctg                                              20

<210> SEQ ID NO 29
<211> LENGTH: 22
<212> TYPE: DNA
<213> ORGANISM: Artificial Sequence
<220> FEATURE:
<223> OTHER INFORMATION: Oligonucleotide

<400> SEQUENCE: 29
ctccaagcca aagtccttag ag                                           22

<210> SEQ ID NO 30
<211> LENGTH: 22
<212> TYPE: DNA
<213> ORGANISM: Artificial Sequence
<220> FEATURE:
<223> OTHER INFORMATION: Oligonucleotide

<400> SEQUENCE: 30
aggagctgtc attagggaca tc                                           22

<210> SEQ ID NO 31
<211> LENGTH: 20
<212> TYPE: DNA
<213> ORGANISM: Artificial Sequence
<220> FEATURE:
<223> OTHER INFORMATION: Oligonucleotide

<400> SEQUENCE: 31
tgatgctgcc attctcattc                                              20

<210> SEQ ID NO 32
<211> LENGTH: 20
<212> TYPE: DNA
<213> ORGANISM: Artificial Sequence
<220> FEATURE:
<223> OTHER INFORMATION: Oligonucleotide

<400> SEQUENCE: 32
cgcagctctc agatttaccc                                              20

<210> SEQ ID NO 33
<211> LENGTH: 20
<212> TYPE: DNA
<213> ORGANISM: Artificial Sequence
<220> FEATURE:
<223> OTHER INFORMATION: Oligonucleotide

<400> SEQUENCE: 33
```

```
ggaggaaggg agaaatgagg                                                 20

<210> SEQ ID NO 34
<211> LENGTH: 20
<212> TYPE: DNA
<213> ORGANISM: Artificial Sequence
<220> FEATURE:
<223> OTHER INFORMATION: Oligonucleotide

<400> SEQUENCE: 34
cacctccaaa agcttccttg                                                 20

<210> SEQ ID NO 35
<211> LENGTH: 19
<212> TYPE: DNA
<213> ORGANISM: Artificial Sequence
<220> FEATURE:
<223> OTHER INFORMATION: Oligonucleotide

<400> SEQUENCE: 35
gctggaggac tcctaggct                                                  19

<210> SEQ ID NO 36
<211> LENGTH: 20
<212> TYPE: DNA
<213> ORGANISM: Artificial Sequence
<220> FEATURE:
<223> OTHER INFORMATION: Oligonucleotide

<400> SEQUENCE: 36
gtcagaagga aacagtccgc                                                 20

<210> SEQ ID NO 37
<211> LENGTH: 20
<212> TYPE: DNA
<213> ORGANISM: Artificial Sequence
<220> FEATURE:
<223> OTHER INFORMATION: Oligonucleotide

<400> SEQUENCE: 37
accaggaagc ttgaatccct                                                 20

<210> SEQ ID NO 38
<211> LENGTH: 20
<212> TYPE: DNA
<213> ORGANISM: Artificial Sequence
<220> FEATURE:
<223> OTHER INFORMATION: Oligonucleotide

<400> SEQUENCE: 38
tccagccact gaagttctga                                                 20

<210> SEQ ID NO 39
<211> LENGTH: 14
<212> TYPE: PRT
<213> ORGANISM: Artificial Sequence
<220> FEATURE:
<223> OTHER INFORMATION: Polypeptide

<400> SEQUENCE: 39

Pro Gly Phe Leu Arg Asp Pro Trp Cys Lys Tyr Gln Met Leu
 1               5                  10
```

```
<210> SEQ ID NO 40
<211> LENGTH: 31
<212> TYPE: PRT
<213> ORGANISM: Artificial Sequence
<220> FEATURE:
<223> OTHER INFORMATION: Polypeptide

<400> SEQUENCE: 40

Asp Arg Gln Ile Lys Ile Trp Phe Gln Asn Arg Arg Met Lys Trp Lys
1               5                   10                  15

Lys Pro Gly Phe Leu Arg Asp Pro Trp Cys Lys Tyr Gln Met Leu
            20                  25                  30
```